(12) United States Patent
Rose et al.

(10) Patent No.: US 11,490,891 B2
(45) Date of Patent: Nov. 8, 2022

(54) LOAD SENSOR FOR CIRCULAR SURGICAL STAPLER

(71) Applicant: Ethicon LLC, Guaynabo, PR (US)

(72) Inventors: Logan R. Rose, Loveland, OH (US); Bradley A. Arnold, Mason, OH (US)

(73) Assignee: Cilag GmbH International, Zug (CH)

( * ) Notice: Subject to any disclaimer, the term of this patent is extended or adjusted under 35 U.S.C. 154(b) by 47 days.

(21) Appl. No.: 16/925,448

(22) Filed: Jul. 10, 2020

(65) Prior Publication Data

US 2022/0008071 A1 Jan. 13, 2022

(51) Int. Cl.
A61B 17/072 (2006.01)

(52) U.S. Cl.
CPC .. *A61B 17/072* (2013.01); *A61B 2017/07257* (2013.01); *A61B 2017/07285* (2013.01); *A61B 2560/0266* (2013.01); *A61B 2562/0247* (2013.01); *A61B 2562/0252* (2013.01); *A61B 2562/0257* (2013.01)

(58) Field of Classification Search
CPC .......... A61B 17/07207; A61B 17/0686; A61B 17/105; A61B 17/1114; A61B 17/115
See application file for complete search history.

(56) References Cited

U.S. PATENT DOCUMENTS

| | | |
|---|---|---|
| 5,205,459 A | 4/1993 | Brinkerhoff et al. |
| 5,271,544 A | 12/1993 | Fox et al. |
| 5,275,322 A | 1/1994 | Brinkerhoff et al. |
| 5,285,945 A | 2/1994 | Brinkerhoff et al. |
| 5,292,053 A | 3/1994 | Bilotti et al. |
| 5,333,773 A | 8/1994 | Main et al. |
| 5,350,104 A | 9/1994 | Main et al. |
| 5,533,661 A | 7/1996 | Main et al. |
| 8,910,847 B2 | 12/2014 | Nalagatla et al. |
| 9,445,816 B2 | 9/2016 | Swayze et al. |
| 9,463,022 B2 | 10/2016 | Swayze et al. |

(Continued)

FOREIGN PATENT DOCUMENTS

| | | |
|---|---|---|
| EP | 3381380 A2 | 10/2018 |
| WO | WO 2019/130087 A1 | 7/2019 |

OTHER PUBLICATIONS

U.S. Appl. No. 16/887,182, entitled "Shaft Attachment Feature for Circular Surgical Stapler," filed on May 29, 2020.

(Continued)

*Primary Examiner* — Nathaniel C Chukwurah
(74) *Attorney, Agent, or Firm* — Frost Brown Todd LLC

(57) ABSTRACT

A surgical circular stapler has a handle assembly, a shaft assembly, a stapling head assembly, and an anvil. Firing the stapler causes the stapling head assembly to drive a plurality of staples in a circular array to secure two lumens of tissue together. The stapling head assembly may further drive a blade to sever any excess tissue interior of the circular array of staples. The stapler further includes one or more sensors that detect the degree to which the anvil is uniformly loaded when compressing tissue prior to firing the stapler. The one or more sensors can provide signals to a processor with various logic rules that can be used to signal to the user whether uniform loading is achieved. In some instances, the signal may be used in an automated fashion to determine if a uniform loading precondition is satisfied such that firing the stapler is enabled.

20 Claims, 19 Drawing Sheets

(56) References Cited

U.S. PATENT DOCUMENTS

| | | | |
|---|---|---|---|
| 9,532,783 B2 | 1/2017 | Swayze et al. | |
| 9,597,081 B2 | 3/2017 | Swayze et al. | |
| 9,713,469 B2 | 7/2017 | Leimbach et al. | |
| 9,907,552 B2 | 3/2018 | Measamer et al. | |
| 9,936,949 B2 | 4/2018 | Measamer et al. | |
| 10,045,780 B2 | 8/2018 | Adams et al. | |
| 10,307,157 B2 | 6/2019 | Miller et al. | |
| 10,709,452 B2 | 7/2020 | DiNardo et al. | |
| 2010/0065609 A1* | 3/2010 | Schwemberger | A61B 17/115 227/180.1 |
| 2012/0016362 A1* | 1/2012 | Heinrich | A61B 17/072 606/41 |
| 2015/0083772 A1 | 3/2015 | Miller et al. | |
| 2015/0272572 A1* | 10/2015 | Overmyer | A61B 17/07207 227/177.1 |
| 2016/0074039 A1* | 3/2016 | Beetel | A61B 17/07207 227/175.1 |
| 2017/0258471 A1 | 9/2017 | DiNardo et al. | |
| 2018/0325517 A1 | 11/2018 | Wingardner et al. | |
| 2018/0368836 A1 | 12/2018 | Auld et al. | |
| 2019/0201136 A1 | 7/2019 | Shelton, IV et al. | |
| 2019/0206569 A1 | 7/2019 | Shelton, IV et al. | |
| 2020/0093487 A1 | 3/2020 | Baber et al. | |
| 2020/0100830 A1 | 4/2020 | Henderson et al. | |
| 2020/0113565 A1 | 4/2020 | Bakos et al. | |
| 2021/0077093 A1 | 3/2021 | Adams et al. | |
| 2021/0077110 A1 | 3/2021 | Adams et al. | |
| 2021/0077112 A1 | 3/2021 | Adams et al. | |

OTHER PUBLICATIONS

U.S. Appl. No. 16/925,387, entitled "Compression and Firing Force Sensor for Circular Surgical Stapler," filed Jul. 10, 2020.

U.S. Appl. No. 63/018,664, entitled "Stabilizer for Surgical Shafts or Cannulas," filed May 1, 2020.

International Search Report and Written Opinion dated Nov. 15, 2021, for International Appl. No. PCT/IB2021/056143, 23 pages.

* cited by examiner

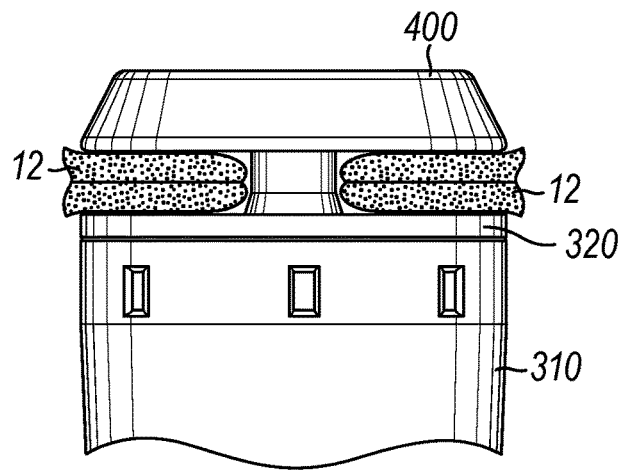
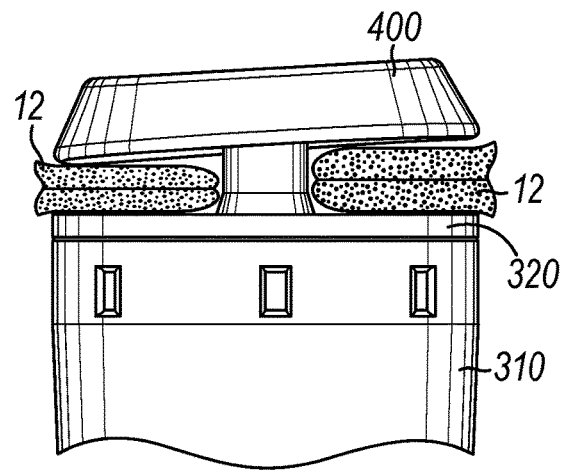
FIG. 9A          FIG. 9B
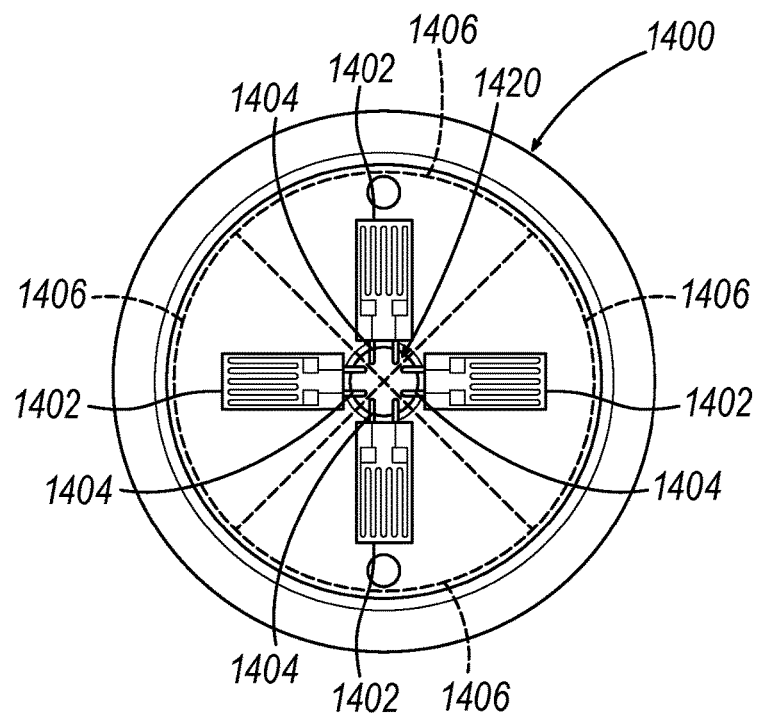
FIG. 10

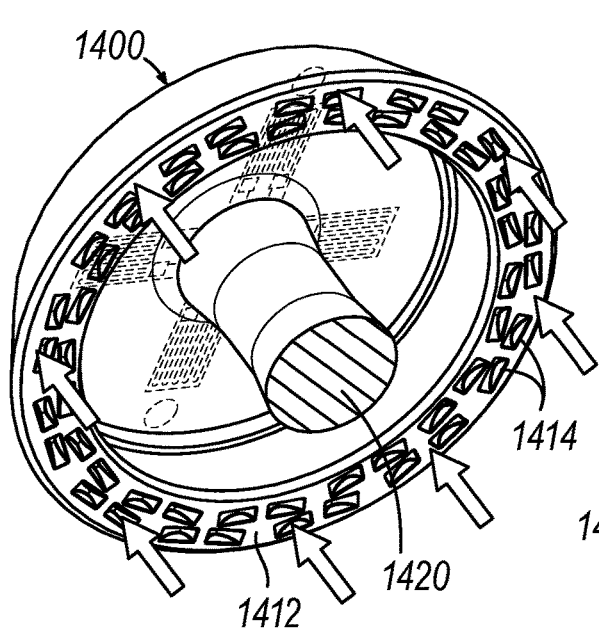
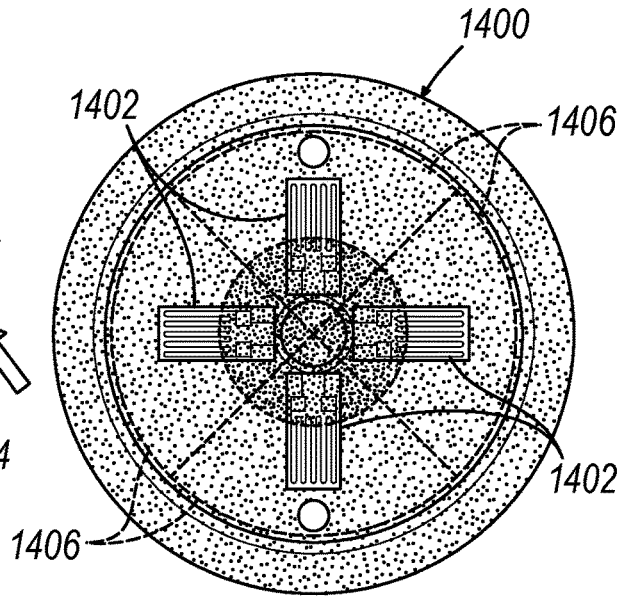
FIG. 11A  FIG. 11B
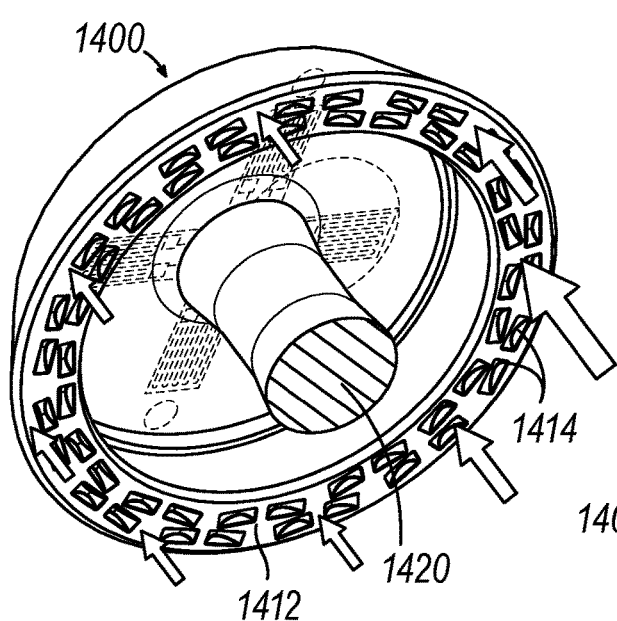
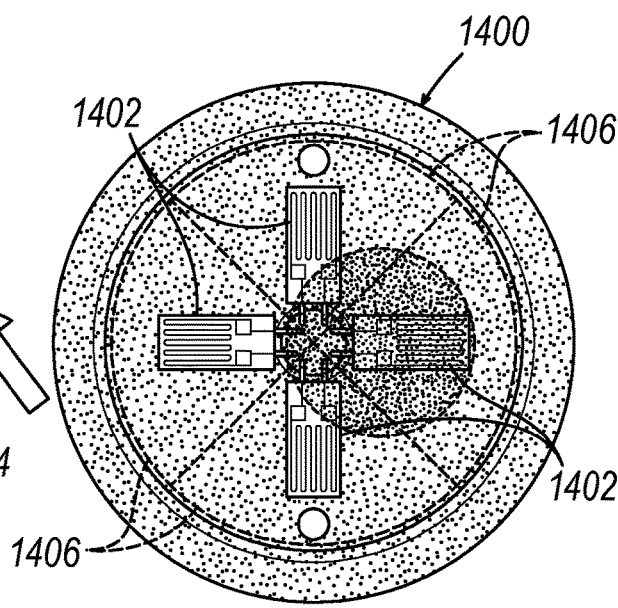
FIG. 12A  FIG. 12B

LOAD SENSOR FOR CIRCULAR SURGICAL STAPLER

BACKGROUND

In some surgical procedures (e.g., colorectal, bariatric, thoracic, etc.), portions of a patient's digestive tract (e.g., the gastrointestinal tract and/or esophagus, etc.) may be cut and removed to eliminate undesirable tissue or for other reasons. Once the tissue is removed, the remaining portions of the digestive tract may be coupled together in an end-to-end anastomosis, an end-to-side anastomosis, or a side-to-side anastomosis. The anastomosis may provide a substantially unobstructed flow path from one portion of the digestive tract to the other portion of the digestive tract, without also providing any kind of leaking at the site of the anastomosis.

One example of an instrument that may be used to provide an anastomosis is a circular stapler. Some such staplers are operable to clamp down on layers of tissue, cut through the clamped layers of tissue, and drive staples through the clamped layers of tissue to substantially seal the layers of tissue together near the severed ends of the tissue layers, thereby joining the two severed ends of the anatomical lumen together. The circular stapler may be configured to sever the tissue and seal the tissue substantially simultaneously. For instance, the circular stapler may sever excess tissue that is interior to an annular array of staples at an anastomosis, to provide a substantially smooth transition between the anatomical lumen sections that are joined at the anastomosis. Circular staplers may be used in open procedures or in endoscopic procedures. In some instances, a portion of the circular stapler is inserted through a patient's naturally occurring orifice.

Examples of circular staplers are described in U.S. Pat. No. 5,205,459, entitled "Surgical Anastomosis Stapling Instrument," issued Apr. 27, 1993; U.S. Pat. No. 5,271,544, entitled "Surgical Anastomosis Stapling Instrument," issued Dec. 21, 1993; U.S. Pat. No. 5,275,322, entitled "Surgical Anastomosis Stapling Instrument," issued Jan. 4, 1994; U.S. Pat. No. 5,285,945, entitled "Surgical Anastomosis Stapling Instrument," issued Feb. 15, 1994; U.S. Pat. No. 5,292,053, entitled "Surgical Anastomosis Stapling Instrument," issued Mar. 8, 1994; U.S. Pat. No. 5,333,773, entitled "Surgical Anastomosis Stapling Instrument," issued Aug. 2, 1994; U.S. Pat. No. 5,350,104, entitled "Surgical Anastomosis Stapling Instrument," issued Sep. 27, 1994; and U.S. Pat. No. 5,533,661, entitled "Surgical Anastomosis Stapling Instrument," issued Jul. 9, 1996; and U.S. Pat. No. 8,910, 847, entitled "Low Cost Anvil Assembly for a Circular Stapler," issued Dec. 16, 2014. The disclosure of each of the above-cited U.S. Patents is incorporated by reference herein.

Some circular staplers may include a motorized actuation mechanism. Examples of circular staplers with motorized actuation mechanisms are described in U.S. Pub. No. 2015/ 0083772, entitled "Surgical Stapler with Rotary Cam Drive and Return," published Mar. 26, 2015; U.S. Pat. No. 9,936, 949, entitled "Surgical Stapling Instrument with Drive Assembly Having Toggle Features," issued Apr. 10, 2018; U.S. Pat. No. 9,907,552, entitled "Control Features for Motorized Surgical Stapling Instrument," issued Mar. 6, 2018; U.S. Pat. No. 9,713,469, entitled "Surgical Stapler with Rotary Cam Drive," issued Jul. 25, 2017; and U.S. Pub. No. 2017/0258471, entitled "Methods and Systems for Performing Circular Stapling," published Sep. 14, 2017. The disclosure of each of the above-cited U.S. Patent Publications is incorporated by reference herein.

While various kinds of surgical stapling instruments and associated components have been made and used, it is believed that no one prior to the inventor(s) has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 9A depicts a side view of an exemplary tissue capture showing tissue compressed between an anvil and stapling head assembly of the circular stapler of FIG. 1, with the tissue under a uniform load;

FIG. 9B depicts a side view of another exemplary tissue capture showing tissue compressed between an anvil and stapling head assembly of the circular stapler of FIG. 1, with the tissue under a non-uniform load;

FIG. 10 depicts a top view of an exemplary anvil configured for use with the circular stapler of FIG. 1, with the anvil having multiple strain gauges;

FIG. 11A depicts a perspective view in cross-section of the anvil of FIG. 10 showing a uniform load condition;

FIG. 11B depicts a top view of the anvil of FIG. 11A showing a graphical representation of the strain measurement when the anvil is under the uniform load condition;

FIG. 12A depicts a perspective view in cross-section of the anvil of FIG. 10 showing a non-uniform load condition;

FIG. 12B depicts a top view of the anvil of FIG. 12A showing a graphical representation of the strain measurement when the anvil is under the non-uniform load condition;

Figure 1:
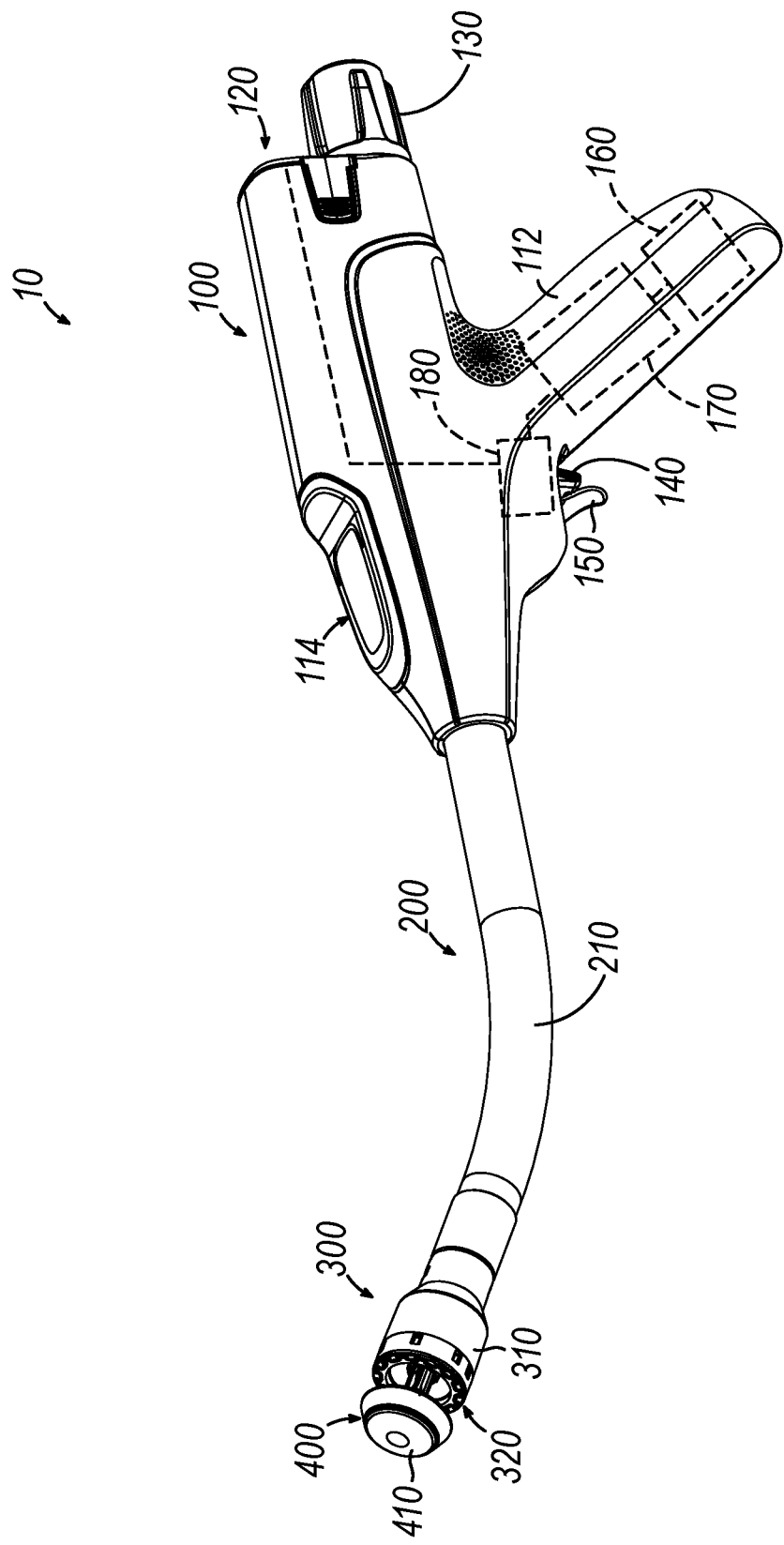
FIG. 1 depicts a perspective view of an exemplary circular surgical stapler.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

For clarity of disclosure, the terms "proximal" and "distal" are defined herein relative to a surgeon, or other operator, grasping a surgical instrument having a distal surgical end effector. The term "proximal" refers to the position of an element arranged closer to the surgeon, and the term "distal" refers to the position of an element arranged closer to the surgical end effector of the surgical instrument and further away from the surgeon. Moreover, to the extent that spatial terms such as "top," "bottom," "upper," "lower," "vertical," "horizontal," or the like are used herein with reference to the drawings, it will be appreciated that such terms are used for exemplary description purposes only and are not intended to be limiting or absolute. In that regard, it will be understood that surgical instruments such as those disclosed herein may be used in a variety of orientations and positions not limited to those shown and described herein.

I. Overview of Exemplary Circular Surgical Stapling Instrument

Figure 2:
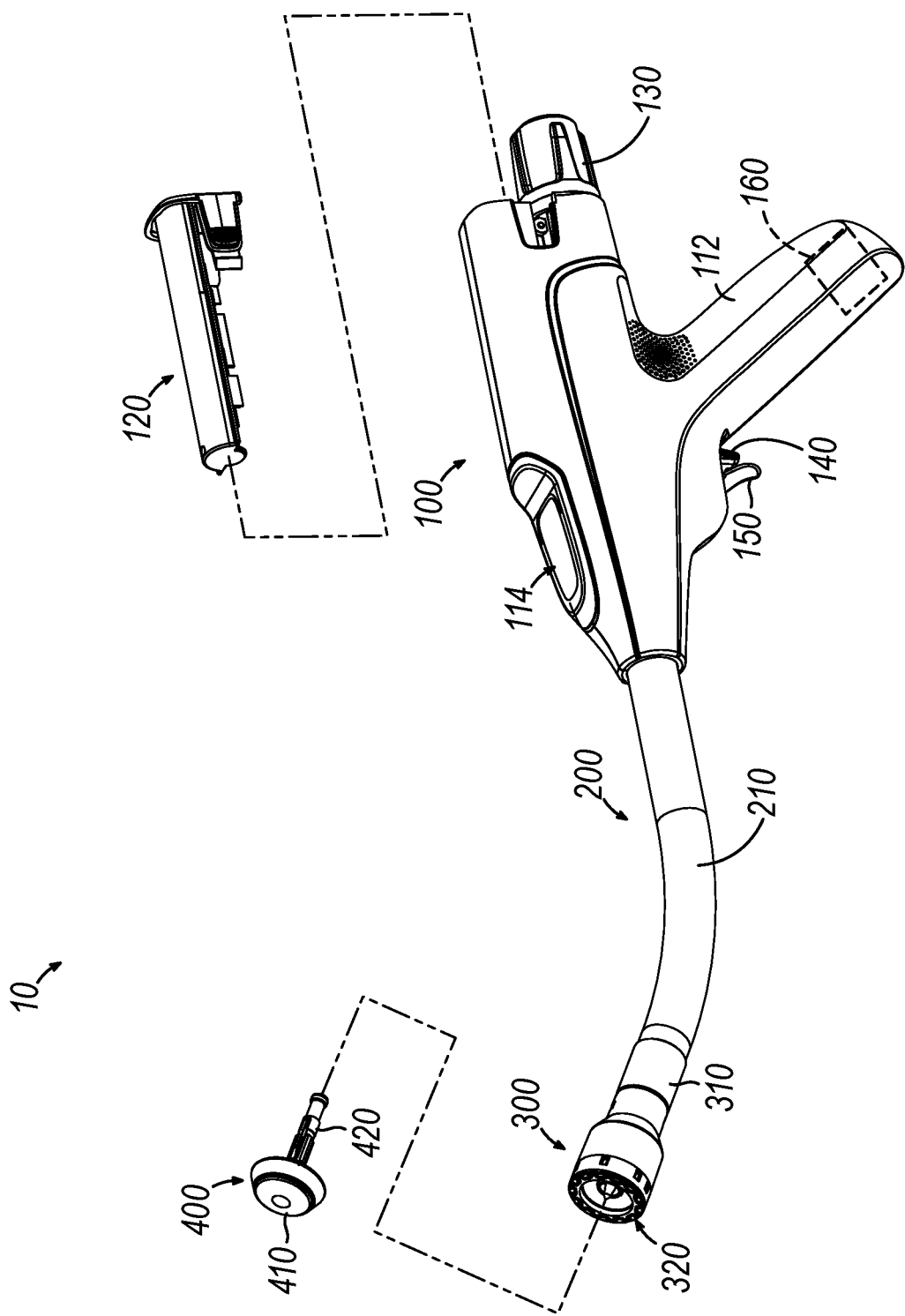
FIG. 2 depicts a perspective view of the circular stapler of FIG. 1, with a battery pack removed from a handle assembly and an anvil removed from a stapling head assembly.

FIGS. 1-2 depict an exemplary circular surgical stapling instrument (10) that may be used to provide an end-to-end, side-to-side, or end-to-side anastomosis between two sections of an anatomical lumen such as a portion of a patient's digestive tract. Instrument (10) of this example includes a body assembly (e.g. a handle assembly (100)), a shaft assembly (200) extending distally from handle assembly (100), a stapling head assembly (300) at a distal end of shaft assembly (200), and an anvil (400) configured to releasably couple and cooperate with stapling head assembly (300) to clamp, staple, and cut tissue. Instrument (10) further includes a removable battery pack (120) operable to provide electrical power to a motor (160) housed within handle assembly (100), as will be described in greater detail below.

Shaft assembly (200) extends distally from handle assembly (100) and includes a preformed bend. In some versions, the preformed bend is configured to facilitate positioning of stapling head assembly (300) within a patient's colon. Various suitable bend angles or radii that may be used will be apparent to those skilled in the art in view of the teachings herein. In some other versions, shaft assembly (200) is straight, such that shaft assembly (200) lacks a preformed bend. Various exemplary components that may be incorporated into shaft assembly (200) will be described in greater detail below.

Stapling head assembly (300) is located at the distal end of shaft assembly (200). As shown in FIGS. 1-2 and as will be described in greater detail below, anvil (400) is configured to removably couple with shaft assembly (200), adjacent to stapling head assembly (300). As will also be described in greater detail below, anvil (400) and stapling head assembly (300) are configured to cooperate to manipulate tissue in three ways, including clamping the tissue, cutting the tissue, and stapling the tissue. A knob (130) at the proximal end of handle assembly (100) is rotatable relative to casing (110) to provide precise clamping of the tissue between anvil (400) and stapling head assembly (300). When a safety trigger (140) of handle assembly (100) is pivoted away from a firing trigger (150) of handle assembly (100), firing trigger (150) may be actuated to thereby provide cutting and stapling of the tissue.

A. Exemplary Anvil

Figure 3:
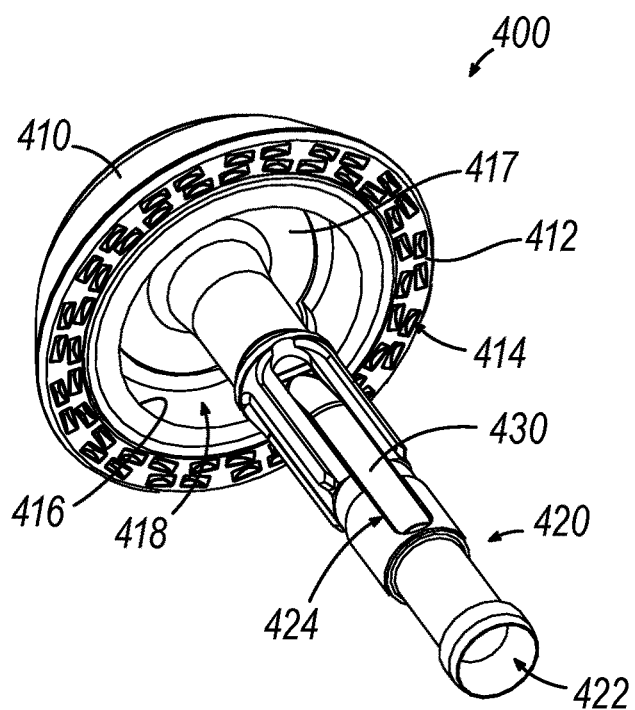
FIG. 3 depicts a perspective view of the anvil of the circular stapler of FIG. 1.

As best seen in FIG. 3, anvil (400) of the present example comprises a head (410) and a shank (420). Head (410)

includes a proximal surface (412) that defines a plurality of staple forming pockets (414). Staple forming pockets (414) are arranged in two concentric annular arrays in the present example. In some other versions, staple forming pockets (414) are arranged in three or more concentric annular arrays. Staple forming pockets (414) are configured to deform staples as the staples are driven into staple forming pockets (414). For instance, each staple forming pocket (414) may deform a generally "U" shaped staple into a "B" shape as is known in the art. Proximal surface (412) terminates at an inner edge (416), which defines an outer boundary of an annular recess (418) surrounding shank (420).

Shank (420) defines a bore (422) and includes a pair of pivoting latch members (430). Latch members (430) are positioned within bore (422) such that the distal ends are positioned at the proximal ends of lateral openings (424), which are formed through the sidewall of shank (420). Lateral openings (424) thus provide clearance for the distal ends and latch shelves (436) to deflect radially outwardly from the longitudinal axis defined by shank (420). However, latch members (430) are configured to resiliently bias the distal ends and latch shelves (436) to pivot radially inwardly toward the longitudinal axis defined by shank (420). Latch members (430) thus act as retaining clips. This allows anvil (400) to be removably secured to an actuatable closure member in the form of a trocar (330) of stapling head assembly (300), as will be described in greater detail below. It should be understood, however, that latch members (436) are merely optional. Anvil (400) may be removably secured to trocar (330) using any other suitable components, features, or techniques.

B. Exemplary Stapling Head Assembly

Figure 4:
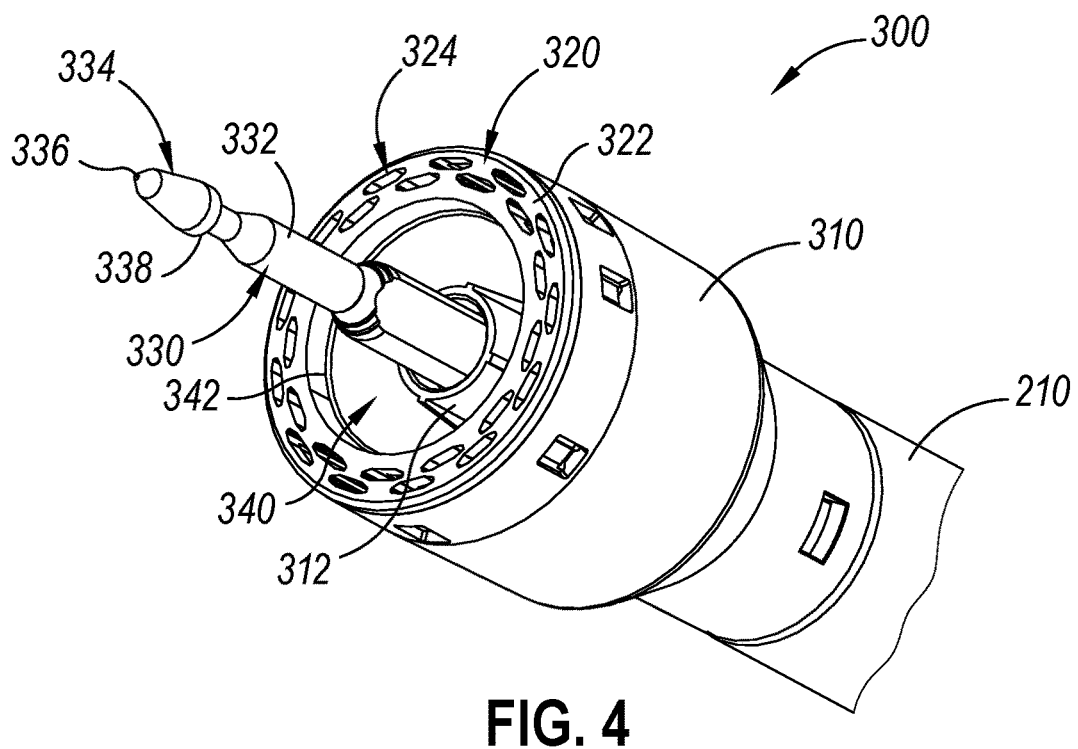
FIG. 4 depicts a perspective view of the stapling head assembly of the circular stapler of FIG. 1.
Figure 5:
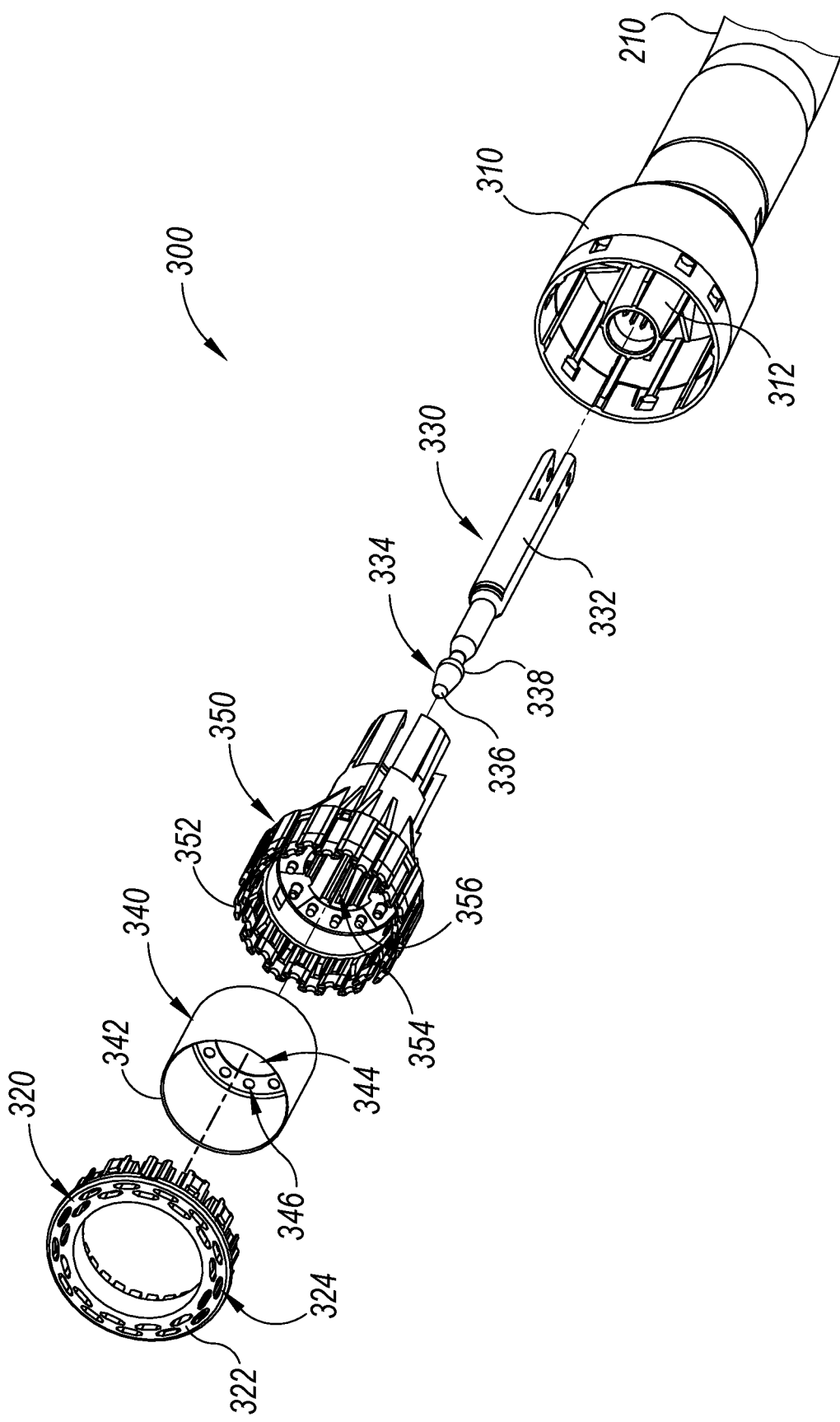
FIG. 5 depicts an exploded perspective view of the stapling head assembly of FIG. 4.

As best seen in FIGS. 4 and 5, stapling head assembly (300) of the present example is coupled to a distal end of shaft assembly (200) and comprises a body member (310) and a staple driver member (350) slidably housed therein. Body member (310) includes a distally extending cylindraceous inner core member (312). Body member (310) is fixedly secured to an outer sheath (210) of shaft assembly (200), and body member (310) and outer sheath (210) thus serve together as a mechanical ground for stapling head assembly (300). In some versions, stapling head assembly (300) may be configured to releasably couple with the distal end of shaft assembly (200), for example as disclosed in U.S. Pat. No. 9,597,081, entitled "Motor Driven Rotary Input Circular Stapler with Modular End Effector," issued Mar. 21, 2017, the disclosure of which is incorporated by reference herein.

Trocar (330) is positioned coaxially within inner core member (312) of body member (310). As will be described in greater detail below, trocar (330) is operable to translate distally and proximally relative to body member (310) in response to rotation of knob (130) relative to casing (110) of handle assembly (100). Trocar (330) comprises a shaft (332) and a head (334). Head (334) includes a pointed tip (336) and an inwardly extending proximal surface (338). Shaft (332) thus provides a reduced outer diameter just proximal to head (334), with surface (338) providing a transition between that reduced outer diameter of shaft (332) and the outer diameter of head (334). While tip (336) is pointed in the present example, tip (336) is not sharp. Tip (336) will thus not easily cause trauma to tissue due to inadvertent contact with tissue. Head (334) and the distal portion of shaft (332) are configured for insertion in bore (422) of anvil (400). Proximal surface (338) and latch shelves (436) have complementary positions and configurations such that latch shelves (436) engage proximal surface (338) when shank (420) of anvil (400) is fully seated on trocar (330). Anvil (400) is thus secured to trocar (330) through a snap fit provided by latch members (430).

Staple driver member (350) is operable to actuate longitudinally within body member (310) in response to activation of motor (160) as will be described in greater detail below. Staple driver member (350) of the present example includes two distally presented concentric annular arrays of staple drivers (352). Staple drivers (352) are arranged to correspond with the arrangement of staple forming pockets (414) of anvil (400). Thus, each staple driver (352) is configured to drive a corresponding staple into a corresponding staple forming pocket (414) when stapling head assembly (300) is actuated. It should be understood that the arrangements of staple drivers (352) and staple forming pockets (414) shown herein may be modified in any suitable manner, provided that staple drivers (352) and staple forming pockets (414) are configured to align with one another to provide proper formation of staples. Staple driver member (350) also defines a bore (354) that is configured to coaxially receive core member (312) of body member (310). An annular array of studs (356) project distally from a distally presented surface surrounding bore (354).

A cylindraceous knife member (340) is coaxially positioned within staple driver member (350). Knife member (340) includes a distally presented, sharp circular cutting edge (342). Knife member (340) is sized such that knife member (340) defines an outer diameter that is smaller than the diameter defined by the inner annular array of staple drivers (352). Knife member (340) also defines an opening that is configured to coaxially receive core member (312) of body member (310). An annular array of openings (346) formed in knife member (340) is configured to complement the annular array of studs (356) of staple driver member (350), such that knife member (340) is fixedly secured to staple driver member (350) via studs (356) and openings (346). By way of example only, studs (356) may be heat staked to knife member (340) using techniques known in the art. Other suitable structural relationships between knife member (340) and stapler driver member (350) will be apparent to those skilled in the art in view of the teachings herein.

A deck member (320) is fixedly secured to a distal end of body member (310). Deck member (320) includes a distally presented deck surface (322) defining two concentric annular arrays of staple openings (324). Staple openings (324) are arranged to correspond with the arrangement of staple drivers (352) and staple forming pockets (414) described above. Thus, each staple opening (324) is configured to provide a path for a corresponding staple driver (352) to drive a corresponding staple through deck member (320) and into a corresponding staple forming pocket (414) when stapling head assembly (300) is actuated. It should be understood that the arrangement of staple openings (324) may be modified to correspond with the arrangement of drivers (352) and staple forming pockets (414) described above. It should also be understood that various structures and techniques may be used to contain staples within stapling head assembly (300) before stapling head assembly (300) is actuated. Such structures and techniques that are used to contain staples within stapling head assembly (300) may prevent the staples from inadvertently falling out through staple openings (324) before stapling head assembly (300) is actuated. Various suitable forms that such structures and techniques may take will be apparent to those skilled in the art in view of the teachings herein.

Referring to FIG. 5, deck member (320) defines an inner diameter that is just slightly larger than the outer diameter defined by knife member (340). Deck member (320) is thus configured to allow knife member (340) to translate distally to a point where cutting edge (342) is distal to deck surface (322).

In some versions of instrument (10) it may be desirable to provide instrument (10) with features that are configured to indicate proper and/or improper attachment of anvil (400) to trocar (330) of stapling head assembly (300). For instance, if anvil (400) is not properly attached to trocar (330), an operator may receive audible and/or tactile feedback indicating improper attachment. Additionally, if anvil (400) is properly attached to trocar (330), an operator may receive audible, tactile, and/or visible feedback indicating proper attachment. In addition, or in the alternative, features may be configured to prevent firing of stapling head assembly (300) unless anvil (400) is properly attached to trocar (330). For instance, if anvil (400) is not properly attached to trocar (330), stapling head assembly (300) may be prevented from firing. If anvil (400) is properly attached to trocar (330), firing of stapling head assembly (300) may be enabled. Such features may include various types of visual indicia, sensors, switches, and the like. By way of example only, such features may include those of the type disclosed in U.S. Pat. No. 10,307,157, entitled "Surgical Stapler with Anvil Seating Detection," issued Jun. 4, 2019, and U.S. Pub. No. 2017/0258471, entitled "Methods and Systems for Performing Circular Stapling," published Sep. 14, 2017, the disclosures of which are incorporated by reference herein.

C. Exemplary Shaft Assembly

Figure 6:
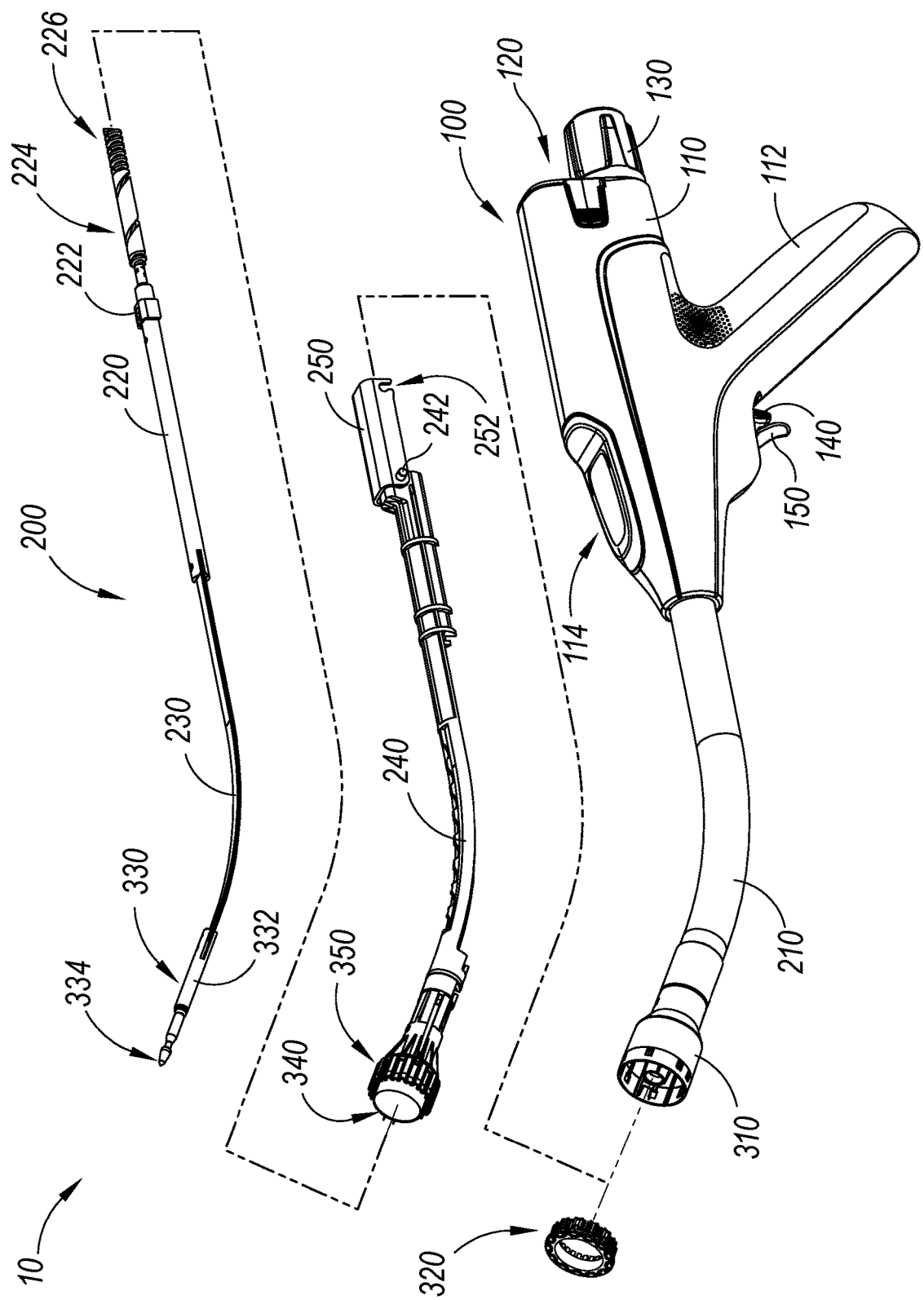
FIG. 6 depicts an exploded perspective view of the circular stapler of FIG. 1, with portions of the shaft assembly shown separated from each other.

FIG. 6 shows various components of shaft assembly (200), which couples components of stapling head assembly (300) with components of handle assembly (100). In particular, and as noted above, shaft assembly (200) includes an outer sheath (210) that extends between handle assembly (100) and body member (310). In the present example, outer sheath (210) is rigid and includes a preformed curved section as noted above.

Shaft assembly (200) further includes a trocar actuation rod (220) and a trocar actuation band assembly (230). The distal end of trocar actuation band assembly (230) is fixedly secured to the proximal end of trocar shaft (332). The proximal end of trocar actuation band assembly (230) is fixedly secured to the distal end of trocar actuation rod (220). It should therefore be understood that trocar (330) will translate longitudinally relative to outer sheath (210) in response to translation of trocar actuation band assembly (230) and trocar actuation rod (220) relative to outer sheath (210). Trocar actuation band assembly (230) is configured to flex such that trocar actuation band assembly (230) may follow along the preformed curve in shaft assembly (200) as trocar actuation band assembly (230) is translated longitudinally relative to outer sheath (210). However, trocar actuation band assembly (230) has sufficient column strength and tensile strength to transfer distal and proximal forces from trocar actuation rod (220) to trocar shaft (332). Trocar actuation rod (220) is rigid. A clip (222) is fixedly secured to trocar actuation rod (220) and is configured to cooperate with complementary features within handle assembly (100) to prevent trocar actuation rod (220) from rotating within handle assembly (100) while still permitting trocar actuation rod (220) to translate longitudinally within handle assembly (100). Trocar actuation rod (220) further includes a coarse helical threading (224) and a fine helical threading (226).

Shaft assembly (200) further includes a stapling head assembly driver (240) that is slidably received within outer sheath (210). The distal end of stapling head assembly driver (240) is fixedly secured to the proximal end of staple driver member (350). The proximal end of stapling head assembly driver (240) is secured to a drive bracket (250) via a pin (242). It should therefore be understood that staple driver member (350) will translate longitudinally relative to outer sheath (210) in response to translation of stapling head assembly driver (240) and drive bracket (250) relative to outer sheath (210). Stapling head assembly driver (240) is configured to flex such that stapling head assembly driver (240) may follow along the preformed curve in shaft assembly (200) as stapling head assembly driver (240) is translated longitudinally relative to outer sheath (210). However, stapling head assembly driver (240) has sufficient column strength to transfer distal forces from drive bracket (250) to staple driver member (350).

D. Exemplary Handle Assembly and User Input Features

As shown in FIG. 1, handle assembly (100) includes a casing (110) having a lower portion that defines an obliquely oriented pistol grip (112) and an upper portion that supports a user interface feature (114) and receives a battery pack (120), as described in greater detail below. Handle assembly (100) further includes several features that are operable to actuate anvil (400) and stapling head assembly (300). In particular, handle assembly (100) includes a rotatable knob (130), a safety trigger (140) a firing trigger (150), a motor (160), and a motor activation module (180). Knob (130) is coupled with trocar actuation rod (220) via a nut (not shown), such that coarse helical threading (224) will selectively engage a thread engagement feature within the interior of the nut; and such that fine helical threading (226) will selectively engage a thread engagement feature within the interior of knob (130). These complementary structures are configured such that trocar actuation rod (220) will first translate proximally at a relatively slow rate, then translate proximally at a relatively fast rate, in response to rotation of knob (130).

It should be understood that when anvil (400) is coupled with trocar (330), rotation of knob (130) will provide corresponding translation of anvil (400) relative to stapling head assembly (300). It should also be understood that knob (130) may be rotated in a first angular direction (e.g., clockwise) to retract anvil (400) toward stapling head assembly (300); and in a second angular direction (e.g., counterclockwise) to advance anvil (400) away from stapling head assembly (300). Knob (130) may thus be used to adjust a gap distance (d) between opposing surfaces (412, 322) of anvil (400) and stapling head assembly (300) until a suitable gap distance (d) has been achieved, for example as shown in FIG. 7C described below.

Firing trigger (150) is operable to activate motor (160) to thereby actuate stapling head assembly (300). Safety trigger (140) is operable to selectively block actuation of firing trigger (150) based on the longitudinal position of anvil (400) in relation to stapling head assembly (300). Handle assembly (100) also includes components that are operable to selectively lock out both triggers (140, 150) based on the position of anvil (400) relative to stapling head assembly (300). For instance, safety trigger (140) may be blocked from rotating from an engaged position to a disengaged position until the position of anvil (400) relative to stapling head assembly (300) is within a predefined range. Accordingly, until the anvil position is within the predefined range, actuation of firing trigger (150) is blocked by safety trigger (140), thereby inhibiting firing of stapling head assembly (300).

Firing trigger (150) of the present example includes an integral actuation paddle (not shown), which may be similar to the paddle disclosed in U.S. Pub. No. 2017/0258471, incorporated by reference above. The paddle is configured to actuate a switch of motor activation module (180) (FIG. 1) when firing trigger (150) is pivoted to a fired position. Motor activation module (180) is in communication with battery pack (120) and motor (160), such that motor activation module (180) is configured to provide activation of motor (160) with electrical power from battery pack (120) in response to the paddle actuating the switch of motor activation module (180). Thus, motor (160) will be activated when firing trigger (150) is pivoted. This activation of motor (160) will actuate stapling head assembly (300) via drive bracket (250), as described in greater detail below. Though not shown, and by way of example only, motor (160) may be operatively coupled with drive bracket (250) via a gearbox coupled with an output shaft of motor (160), a rotary cam member coupled with an output shaft of the gearbox, and a cam follower coupled with the rotary cam member, for example as disclosed in U.S. Pub. No. 2017/0258471, incorporated by reference above.

As best shown in FIGS. 1-2, handle assembly (100) is further configured to releasably receive a battery pack (120) operable to provide electrical power to motor (160), as noted above. It should be understood that battery pack (120) and handle assembly (100) may have complementary electrical contacts, pins and sockets, and/or other features that provide paths for electrical communication from battery pack (120) to electrically powered components in handle assembly (100) when battery pack (120) is coupled with handle assembly (100). It should also be understood that, in some versions, battery pack (120) may be unitarily integrated within handle assembly (100) such that battery back (120) cannot be removed from handle assembly (100).

E. Exemplary Anastomosis Procedure with Circular Stapling Instrument

FIGS. 7A-7E show instrument (10) being used to form an anastomosis (70) between two tubular anatomical structures (20, 40). By way of example only, the tubular anatomical structures (20, 40) may comprise sections of a patient's esophagus, sections of a patient's colon, other sections of the patient's digestive tract, or any other tubular anatomical structures. In some versions, one or more diseased portions of a patient's colon are removed, with the tubular anatomical structures (20, 40) of FIGS. 7A-7E representing the remaining severed portions of the colon.

Figure 7A:
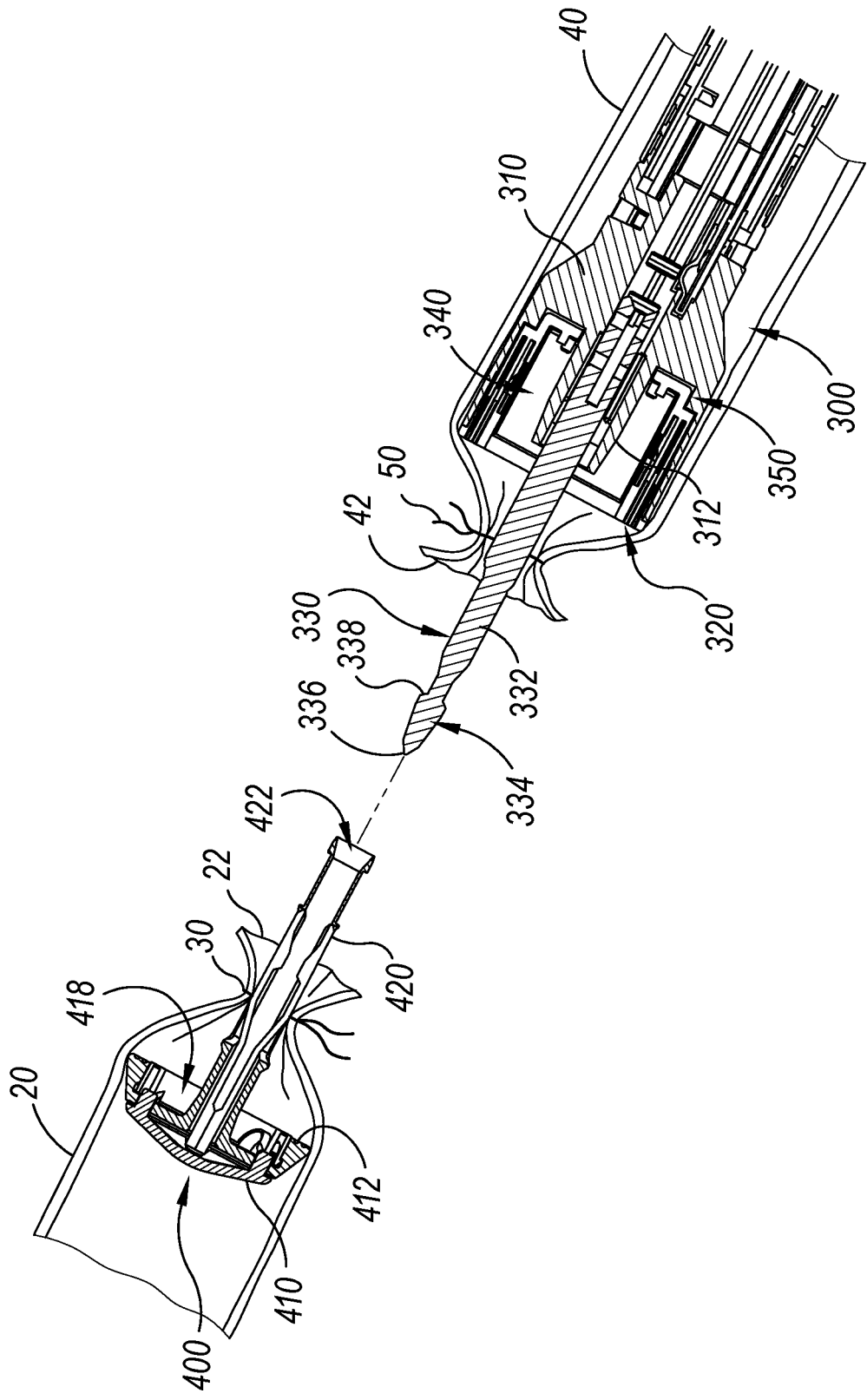
FIG. 7A depicts a cross-sectional side view of the anvil of FIG. 3 positioned within a first section of a digestive tract and the stapling head assembly of FIG. 4 positioned in a second section of the digestive tract, with the anvil separated from the stapling head assembly.

As shown in FIG. 7A, anvil (400) is positioned in one tubular anatomical structure (20) and stapling head assembly (300) is positioned in another tubular anatomical structure (40). In versions where tubular anatomical structures (20, 40) comprise sections of a patient's colon, stapling head assembly (300) may be inserted via the patient's rectum. It should also be understood that the procedure depicted in FIGS. 7A-7E is an open surgical procedure, though the procedure may instead be performed laparoscopically. Various suitable ways in which instrument (10) may be used to form an anastomosis (70) in a laparoscopic procedure will be apparent to those skilled in the art in view of the teachings herein.

As shown in FIG. 7A, anvil (400) is positioned in tubular anatomical structure (20) such that shank (420) protrudes from the open severed end (22) of tubular anatomical structure (20). In the present example, purse-string suture (30) is provided about a mid-region of shank (420) to generally secure the position of anvil (400) in tubular anatomical structure (20). In some other variations, purse-string suture (30) is tightened around the proximal end of shank (420). In some such variations, the proximal end of shank (420) may include a notch or other feature to securely capture purse-string suture (30). Continuing with the present example, stapling head assembly (300) is positioned in tubular anatomical structure (40) such that trocar (330) protrudes from the open severed end (42) of tubular anatomical structure (20). A purse-string suture (50) is provided about a mid-region of shaft (332) to generally secure the position of stapling head assembly (300) in tubular anatomical structure (40). Stapling head assembly (300) is then urged distally to ensure that stapling head assembly (300) is fully seated at the distal end of tubular anatomical structure (40).

Figure 7B:
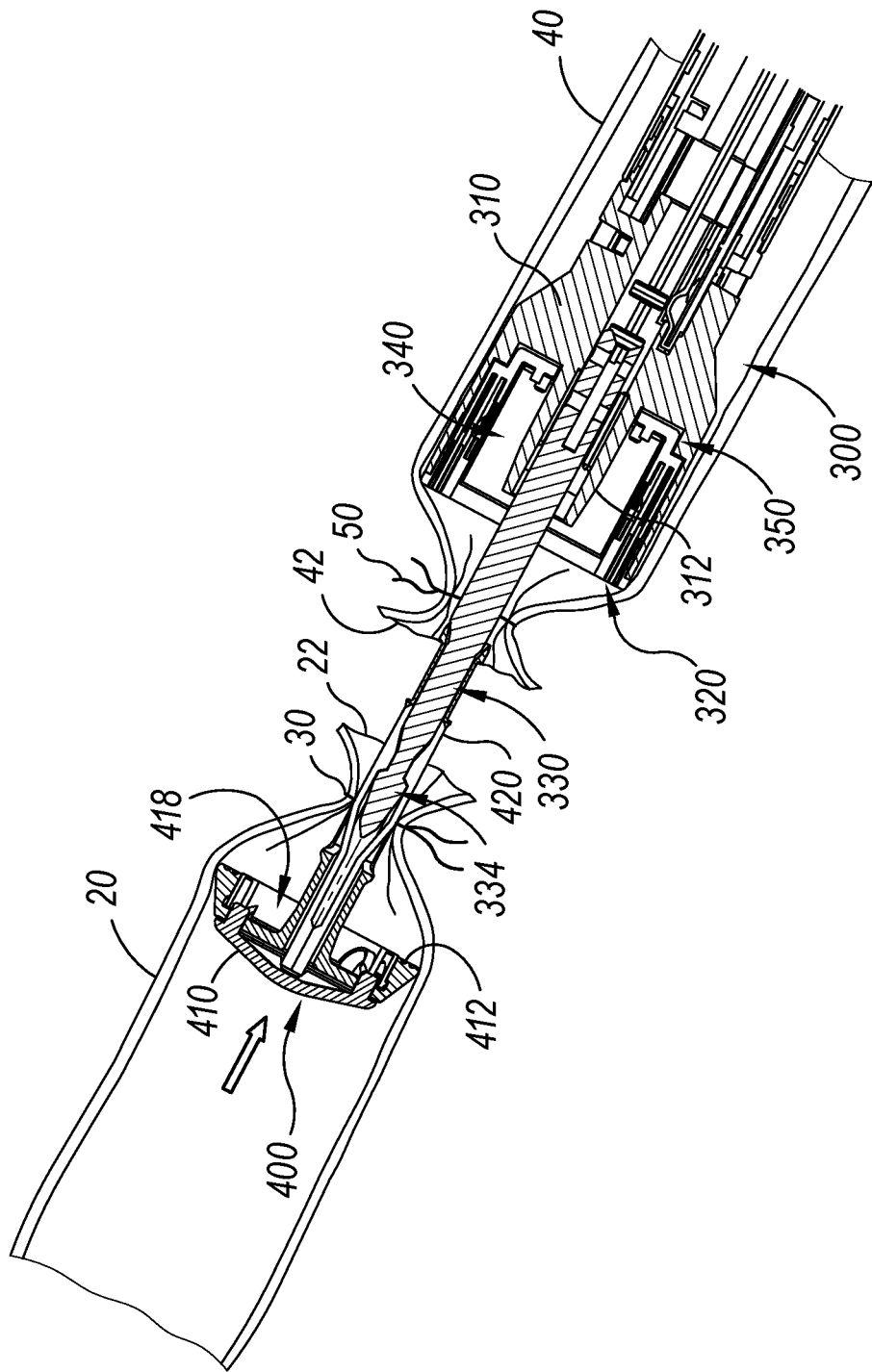
FIG. 7B depicts a cross-sectional side view of the anvil of FIG. 3 positioned within the first section of the digestive tract and the stapling head assembly of FIG. 4 positioned in the second section of the digestive tract, with the anvil secured to the stapling head assembly.
Figure 7C:
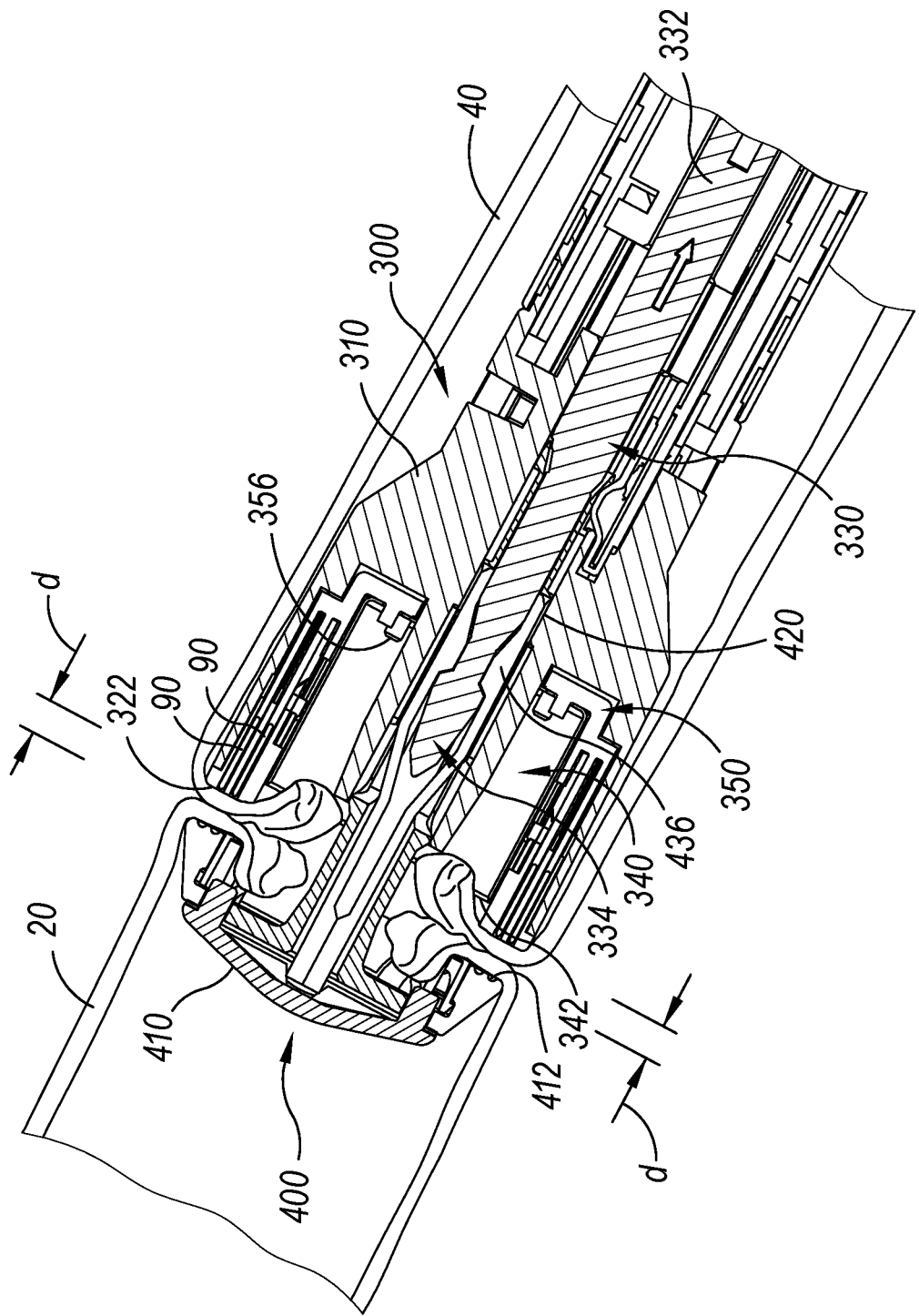
FIG. 7C depicts a cross-sectional side view of the anvil of FIG. 3 positioned within the first section of the digestive tract and the stapling head assembly of FIG. 4 positioned in the second section of the digestive tract, with the anvil retracted toward the stapling head assembly to thereby clamp tissue between the anvil and the stapling head assembly.

Next, anvil (400) is secured to trocar (330) by inserting trocar (330) into bore (422) as shown in FIG. 7B. Latch members (430) engage head (334) of trocar (330), thereby providing a secure fit between anvil (400) and trocar (330). The operator then rotates knob (130) while holding casing (110) stationary via pistol grip (112). This rotation of knob (130) causes trocar (330) and anvil (400) to retract proximally. As shown in FIG. 7C, this proximal retraction of trocar (330) and anvil (400) compresses the tissue of tubular anatomical structures (20, 40) between surfaces (412, 322) of anvil (400) and stapling head assembly (300). As this occurs, the operator may observe the tactile resistance or feedback via knob (130) while turning knob (130), with such tactile resistance or feedback indicating that the tissue is being compressed. As the tissue is being compressed, the operator may visually observe the position of an indicator needle (522) within a user interface feature (114) of handle assembly (100) to determine whether the gap distance (d) between opposing surfaces (412, 322) of anvil (400) and stapling head assembly (300) is appropriate; and make any necessary adjustments via knob (130).

Figure 7D:
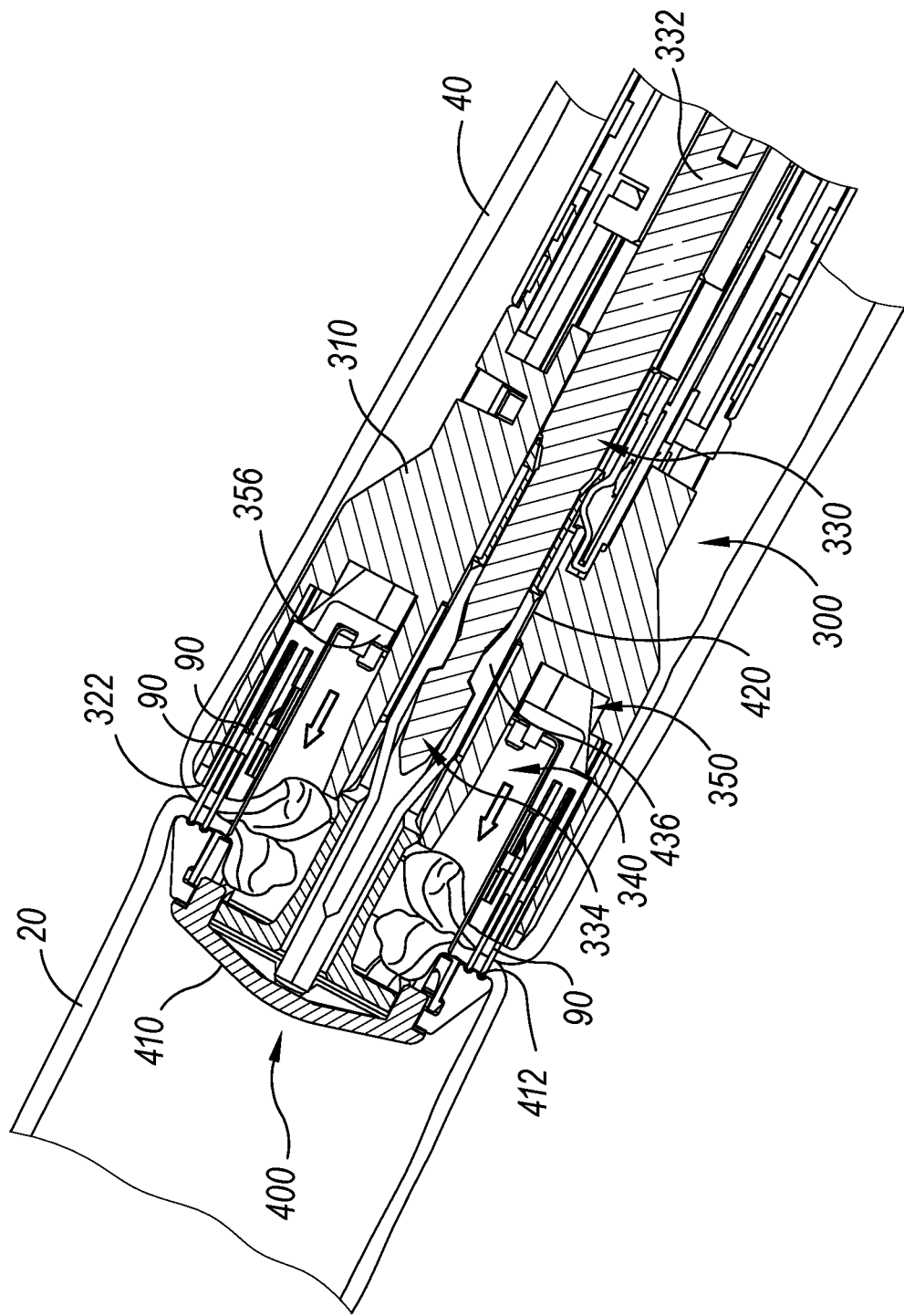
FIG. 7D depicts a cross-sectional side view of the anvil of FIG. 3 positioned within the first section of the digestive tract and the stapling head assembly of FIG. 4 positioned in the second section of the digestive tract, with the stapling head assembly actuated to sever and staple the clamped tissue.

Once the operator has appropriately set the gap distance (d) via knob (130), the operator pivots safety trigger (140) toward pistol grip (112) to enable actuation of firing trigger (150). The operator then pivots firing trigger (150) toward pistol grip (112), thus causing paddle (not shown) to actuate the switch of motor activation module (180) and thereby activate motor (160) to rotate. This rotation of motor (160) causes actuation (or "firing") of stapling head assembly (300) by actuating drive bracket (250) distally to thereby drive knife member (340) and staple driver member (350) distally, as shown in FIG. 7D. As knife member (340) translates distally, cutting edge (342) of knife member (340) cuts excess tissue that is positioned within annular recess (418) of anvil (400) and the interior of knife member (340).

As shown in FIG. 3, anvil (400) of the present example includes a breakable washer (417) positioned within annular recess (418). This washer (417) is broken by knife member (340) when the knife member (340) completes a full distal range of motion from the position shown in FIG. 7C to the position shown in FIG. 7D. Features of stapler (10) may be configured to provide an increasing mechanical advantage as knife member (340) reaches the end of its distal movement, thereby providing greater force by which to break the washer (417). Of course, the breakable washer (417) may be omitted entirely in some versions. In versions where washer (417) is included, it should be understood that washer (417) may also serve as a cutting board for knife member (340) to assist in cutting of tissue.

As staple driver member (350) translates distally from the position shown in FIG. 7C to the position shown in FIG. 7D, staple driver member (350) drives staples (90) through the tissue of tubular anatomical structures (20, 40) and into staple forming pockets (414) of anvil (400). Staple forming pockets (414) deform the driven staples (90) into a "B" shape or a three-dimensional shape, for example, such that the formed staples (90) secure the ends of tissue together, thereby coupling tubular anatomical structure (20) with tubular anatomical structure (40).

Figure 7E:
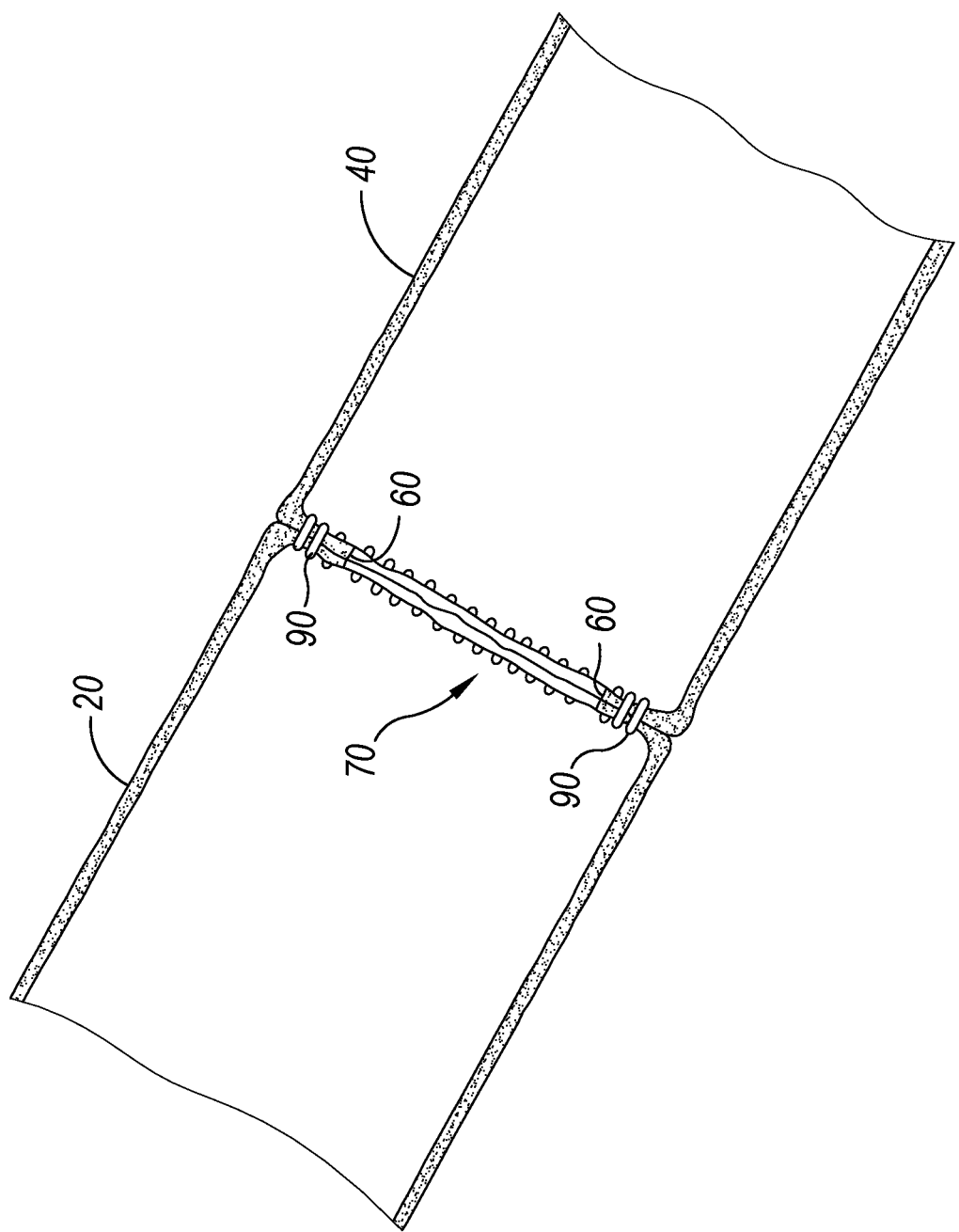
FIG. 7E depicts a cross-sectional side view of the first and second sections of the digestive tract of FIG. 7A joined together at an end-to-end anastomosis.

After the operator has actuated stapling head assembly (300) as shown in FIG. 7D, the operator rotates knob (130) to drive anvil (400) distally away from stapling head assembly (300), increasing the gap distance (d) to facilitate release of the tissue between surfaces (412, 322). The operator then removes instrument (10) from the patient, with anvil (400) still secured to trocar (330). Referring back to the example where the tubular anatomical structures (20, 40) comprise sections of a patient's colon, instrument (10) may be removed via the patient's rectum. With instrument (10) removed, the tubular anatomical structures (20, 40) are left secured together by two annular arrays of staples (90) at an anastomosis (70) as shown in FIG. 7E. The inner diameter of the anastomosis (70) is defined by the severed edge (60) left by knife member (340).

F. Exemplary User Interface Feature of Handle Assembly

Figure 8:
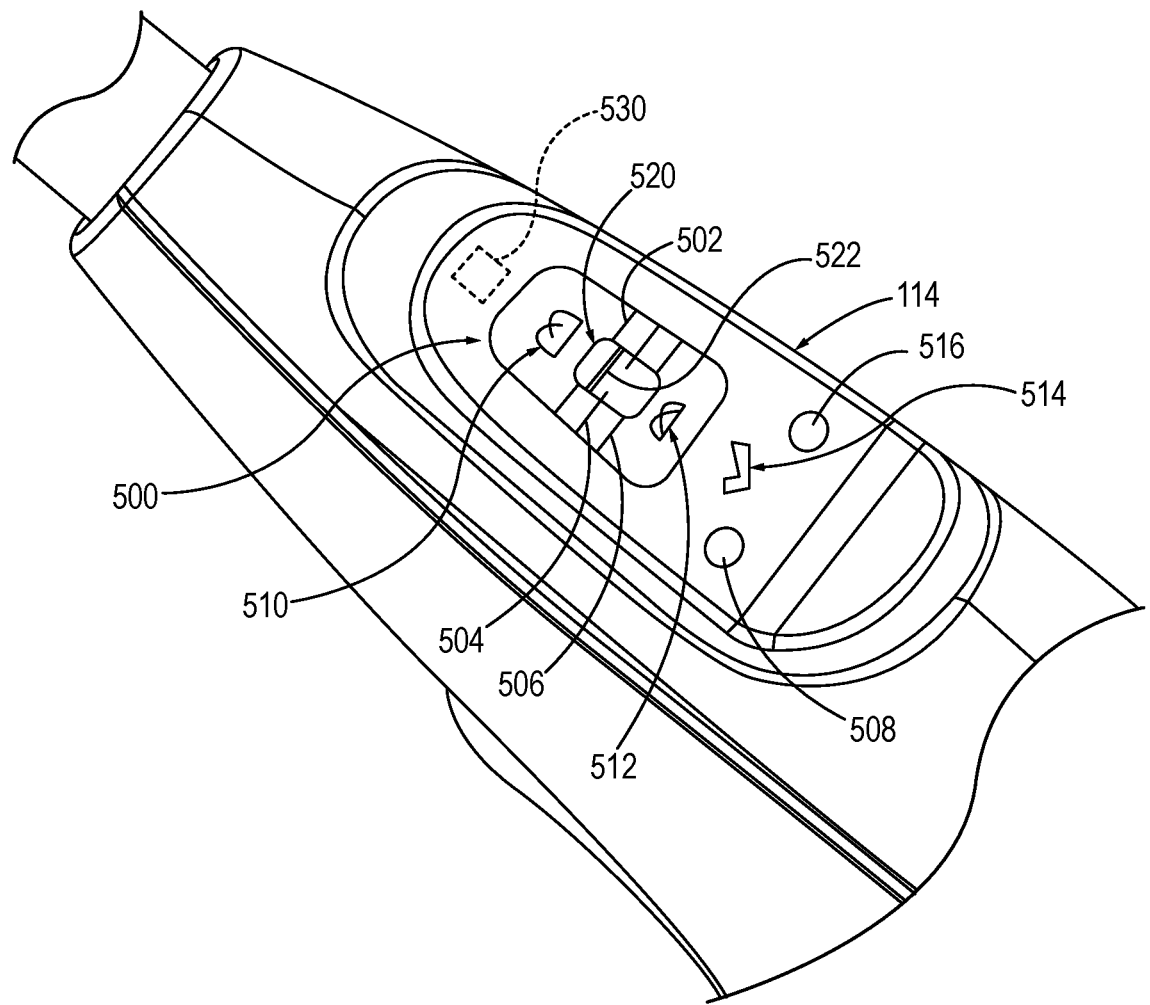
FIG. 8 depicts a perspective view of a user interface feature of the handle assembly of the circular stapler of FIG. 1.

As shown best in FIG. 8, handle assembly (100) of surgical stapling instrument (10) further includes a user interface feature (114) configured to provide the operator with visual feedback indicating the positioning of anvil (400) in relation to stapling head assembly (300) during a surgical procedure. The operator may thus observe user interface feature (114) while rotating knob (130) to confirm whether a suitable gap distance (d) between anvil (400) and stapling head assembly (300) has been achieved.

User interface feature (114) of the present example includes a graphical indicator (500), which includes fixed linear indicia (502, 504, 506), graphical representations (510, 512) of staples, and a checkmark graphic (514). User interface feature (114) further defines a window (520) through which an indicator needle (522) may be viewed. In some variations, user interface feature (114) further includes a field (530) that may indicate a diameter associated with the size of stapling head assembly (300), the size of staples in stapling head assembly (300), the size of the gap defined between anvil (400) and stapling head assembly (300), and/or other information. By way of example only, field (530) may indicate a stapling head assembly (300) size of 23 mm, 25 mm, 29 mm, or 31 mm.

As the operator rotates knob (130) to adjust the longitudinal position of anvil (400) relative to stapling head assembly (300), the operator may observe the position of indicator needle (522) through window (520). Initially, indicator needle (522) may be positioned at or near the distal end of window (520). As anvil (400) continues to move proximally, indicator needle (522) will eventually move proximally relative to window (520). The operator may view the position of indicator needle (522) in relation to fixed linear indicia (502, 504, 506). The distal-most and proximal-most indicia (502, 506) may represent the boundaries of a "green zone," which is the acceptable range of distance between anvil (400) and stapling head assembly (300) for successful actuation of stapling head assembly (300). Thus, if indicator needle (522) is distal to distal-most indicia (502), the distance between anvil (400) and stapling head assembly (300) is too large; and if indicator needle (522) is proximal to proximal-most indicia (506), the distance between anvil (400) and stapling head assembly (300) is too small. Indicia (504) is longitudinally positioned between indicia (502, 506). Graphical representation (510) represents a relatively tall formed staple (e.g., suitable for use in relatively thick tissue); while graphical representation (512) represents a relatively short formed staple (e.g., suitable for use in relatively thin tissue). Graphical representations (510, 512) may thus facilitate the operator's decision, based on tissue observations or otherwise, on whether and how to achieve a desired formed staple height by selecting an appropriate corresponding spatial relationship between indicator needle (522) and indicia (502, 504, 506).

In the present example, window (520) is illuminated via a light emitting diode (LED) (not shown), further facilitating viewing of indicator needle (522) in window (520). In addition, checkmark graphic (514) is illuminated via another LED (not shown) when stapling head assembly (300) completes a stapling and cutting cycle. Thus, the operator may further rely on illumination of checkmark graphic (514) to confirm that the stapling and cutting cycle is complete, to thereby verify that it is safe to advance anvil (400) distally away from the anastomosis (70) to release the tissue and thereafter remove instrument (10) from the patient.

Circular surgical stapling instrument (10) may be further configured and operable in accordance with at least some of the teachings of U.S. Pub. No. 2017/0258471, incorporated by reference above.

II. Exemplary Load Sensing

As mentioned above, some features provide a way to confirm that the anvil is connected with the trocar, and other features provide a way to gauge the degree of staple formation based on the distance between the underside anvil surface having the stapling forming pockets and the deck surface having the staple openings. In some instances, it would be separately or additionally desirable to have the ability to confirm, prior to firing or driving staples, that the circumferential load being applied to the tissue is uniform or substantially uniform. In at least some versions, substantially uniform means that the load is within an acceptable level of variability where the quality of stapling head assembly (300) actuation avoids defects such as malformed staples; or where washer (417) is not completely broken by for knife member (340). Substantial uniformity in this respect will be apparent to those skilled in the art in view of the teachings herein.

Referring to FIGS. 9A and 9B, each show a cross-section view of a distal region showing anvil (400) and deck member (320) with tissue (12) compressed between anvil (400) and deck member (320). FIG. 9A depicts a condition or state of uniform loading applied to tissue (12). As shown in FIG. 9A, the thickness of tissue (12) is consistent through the circumferential area of contact. This consistent thickness of tissue (12) can be a condition that promotes uniformity of the load placed on tissue (12). As shown in FIG. 9B, in some other instances, tissue (12) captured between anvil (400) and deck member (320) may not be of a consistent thickness through the circumferential area of contact. Such inconsistency can result in a non-uniform load placed on tissue (12). Performing a stapling and cutting action under a non-uniform load condition or state can result in defects such as incomplete washer cuts and/or malformed staples.

The teachings below describe various ways to assess the loading state of the tissue between the anvil and the deck member of the stapling head assembly to determine whether a uniformity condition exists for the load. While the teachings below are disclosed in the context of circular surgical staplers, it will be appreciated that such teachings may be applied to other types of surgical staplers as well. By way of example only, such other staplers may include right-angle surgical staplers of the type disclosed in U.S. Pat. No. 10,045,780, entitled "Method of Applying Staples in Lower Anterior Bowel Resection," issued Aug. 14, 2018, the disclosure of which is incorporated by reference herein.

A. Exemplary Strain Gauges

FIG. 10 illustrates an exemplary anvil (1400) that is configured for use with instrument (10). For instance, in some versions anvil (1400) replaces anvil (400). With the exception of the features noted below, anvil (1400) is otherwise the same as anvil (400) such that the description herein of anvil (400) applies equally to anvil (1400).

Anvil (1400) is configured with one or more sensors, which in the present example comprise strain gauges (1402). Strain gauges (1402) are connected with a top or distal surface of anvil (1400) and are configured to detect and measure the strain imparted on anvil (1400) when anvil (1400) compresses tissue (12) against deck member (320). As shown in the present example, three or more sensors or strain gauges (1402) are used, and in this case four strain gauges (1402). Additionally, in the present example, strain gauges (1402) are spaced equally apart from one another. Each strain gauge (1402) has a pair of wires or conductors (1404) that connect with each respective strain gauge (1402) and are then routed through shank (1420) of anvil (1400).

The placement of strain gauges (1402) relative to anvil (1400), define multiple loading zones (1406). In the present example, the four strain gauges (1402) define four loading zones (1406) where each loading zone (1406) represents the area or region surrounding and including a respective strain gauge (1402).

FIGS. 11A and 11B illustrate an example of anvil (1400) applying a load to tissue in a uniform manner. In the application of force on the tissue, it is apparent that an equal and opposite force is applied by the tissue onto proximal surface (1412) of anvil (1400). As shown in FIG. 11A, force arrows are shown to graphically illustrate the force being placed upon the proximal surface (1412) of anvil (1400). These force arrows are intended, by way of example only, to illustrate the magnitude of the force based on the force arrows size and weight. As shown in FIG. 11A, the force arrows are consistent along the circumference of proximal surface (1412) of anvil (1400), thereby indicating that in FIG. 11A a uniform load is applied to the tissue.

FIG. 11B shows a top view of anvil (1400) in a graphic manner to illustrate that under the uniform load condition or state of FIG. 11A, strain gauges (1402) detect and measure consistent strains within each of the respective loading zones (1406) defined by the respective strain gauges (1402).

FIGS. 12A and 12B illustrate an example of anvil (1400) applying a load to tissue in a non-uniform manner. In the application of force on the tissue, it is apparent that an equal and opposite force is applied by the tissue onto proximal surface (1412) of anvil (1400) as mentioned above. As shown in FIG. 12A, force arrows are shown to graphically illustrate the force being placed upon the proximal surface (1412) of anvil (1400). These force arrows are intended, by way of example only, to illustrate the magnitude of the force based on the force arrows size and weight. As shown in FIG. 12A, the force arrows are inconsistent along the circumference of proximal surface (1412) of anvil (1400), thereby indicating that in FIG. 12A a non-uniform load is applied to the tissue. For instance, in the present example of FIG. 12A, one of landing zones (1406) is experiencing a greater amount of force or load than the other three landing zones (1406) as shown by the graphical force arrows size and weight.

FIG. 12B shows a top view of anvil (1400) in a graphic manner to illustrate that under the non-uniform load condition or state of FIG. 12A, strain gauges (1402) detect and measure different strains across loading zones (1406) defined by respective strain gauges (1402). For instance, as shown in FIG. 12B and consistent with FIG. 12A, the load within one loading zone (1406) is much greater than the load in the other three loading zones (1406) signifying a non-uniform loading condition or state.

In one example of anvil (1400) as depicted in FIGS. 11A-12B, in each instance a total force applied to tissue (12) by anvil (1400) is 90 pounds-force. However, this total force results from a uniform loading in the example of FIGS. 11A and 11B, while it results from a non-uniform or uneven loading in the example of FIGS. 12A and 12B. This illustration shows why considering only the total load on the tissue can give a user of instrument (10) the belief or suggestion that the target load is as desired and instrument (10) is ready to fire and drive staples, when in reality there may be uneven or non-uniform loading that can be problematic in terms of stapling and cutting defects. As such, considering not only the total load, but also how that total load is distributed provides better information that can give the user of instrument (10) a higher degree of confidence that the procedure will be executed without defects.

Figure 16A:
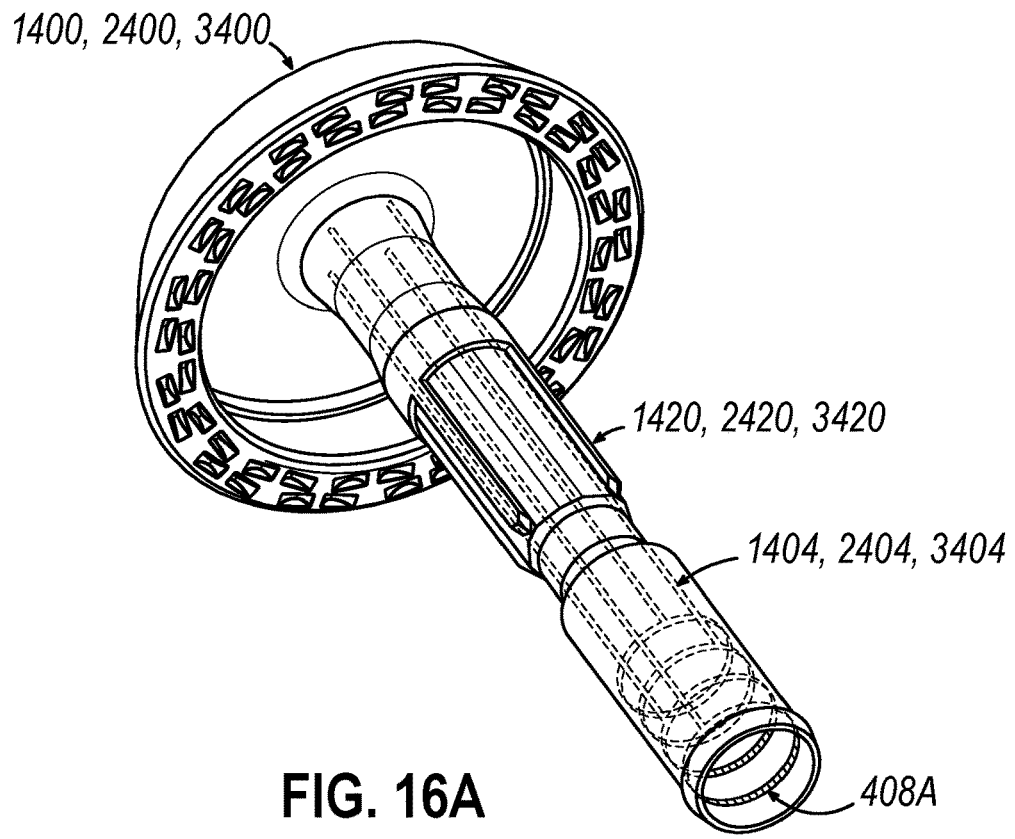
FIG. 16A depicts a perspective view in cross-section of an exemplary anvil configured for use with the circular stapler of FIG. 1, the anvil including contacts for transmitting signals from the anvil to the remainder of the stapler.
Figure 16B:
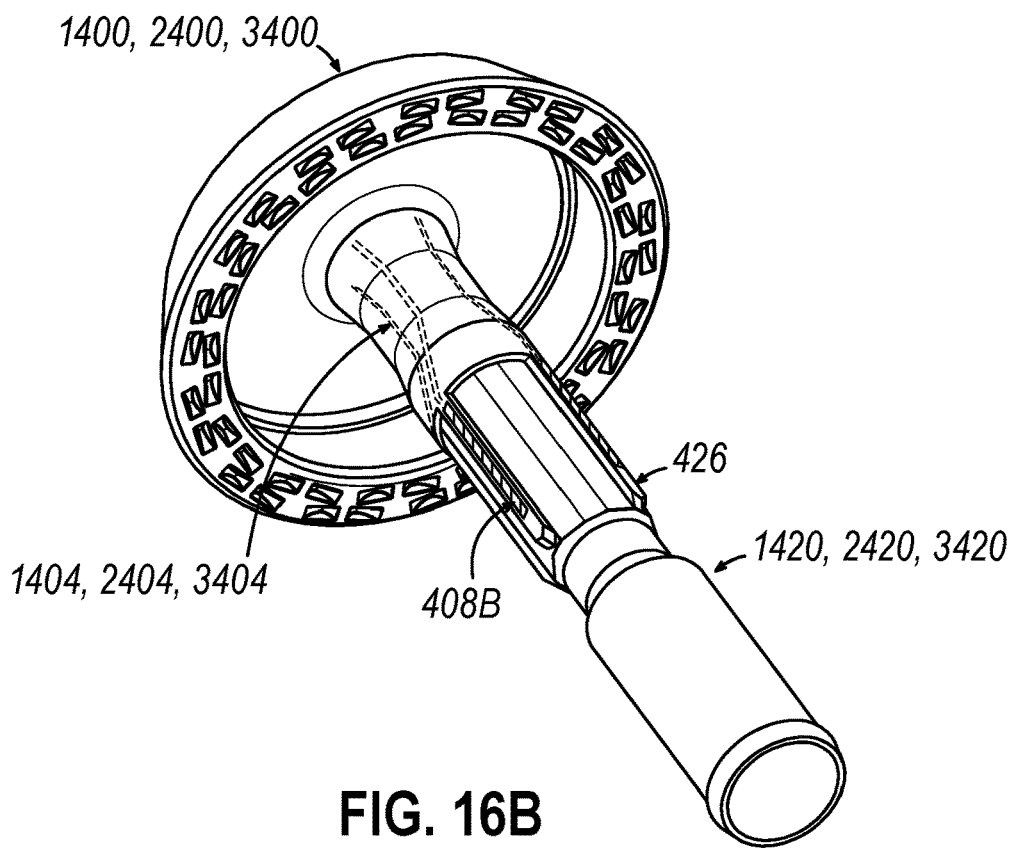
FIG. 16B depicts a perspective view of another exemplary anvil configured for use with the circular stapler of FIG. 1, the anvil including contacts for transmitting signals from the anvil to the remainder of the stapler.

As mentioned above, wires or conductors (1404) connect with respective strain gauges (1402). As will be described in greater detail below, wires (1404) extend and connect with respective contacts (408A, 408B) (FIGS. 16A and 16B). In this manner, when anvil (1400) connects with trocar (330) of stapling head assembly (300), contacts (408A, 408B) are in contact with corresponding contacts within stapling head assembly such that the signal originating at strain gauges (1402) is transmittable from anvil (1400) to the remainder of instrument (10). Again, further details regarding the signal transmission through instrument (10) will be described below.

B. Exemplary Proximity Sensors

Figure 13A:
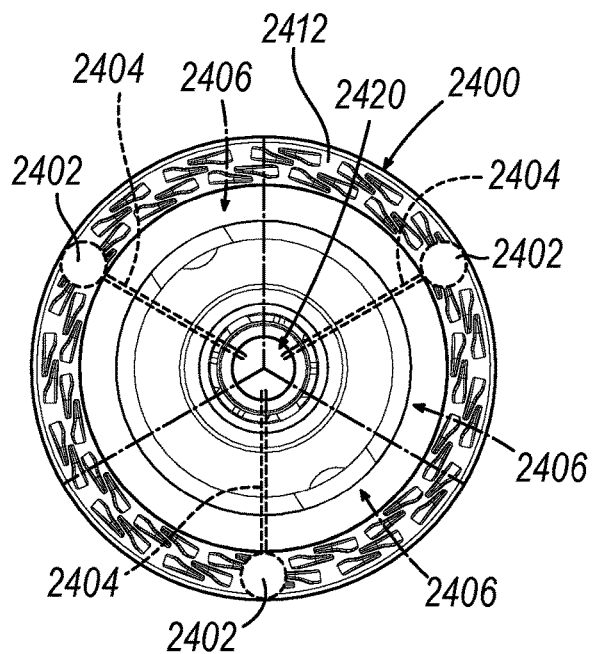
FIG. 13A depicts a bottom view of another exemplary anvil configured for use with the circular stapler of FIG. 1, with the anvil having multiple proximity sensors.

FIG. 13A depicts an exemplary anvil (2400) configured for use with instrument (10). For instance, in some versions anvil (2400) replaces anvil (400). With the exception of the features noted below, anvil (2400) is otherwise the same as anvil (400) such that the description herein of anvil (400) applies equally to anvil (2400).

Anvil (2400) is configured with one or more sensors, which in the present example comprise hall effect or proximity sensors (2402). Proximity sensors (2402) are connected with proximal surface (2412) of anvil (2400) and are configured to detect and measure the distance between proximal surface (2412) and deck surface (322) of deck member (320) when anvil (2400) compresses tissue (12)

against deck member (320). As shown in the present example, three or more sensors or proximity sensors (2402) are used, and in this case three proximity sensors (2402). Additionally, in the present example, proximity sensors (2402) are spaced equally apart from one another. Each proximity sensor (2402) has a pair of wires or conductors (2404) that connect with each respective proximity sensor (2402) and are then routed along top side of anvil (2400) and through shank (2420) of anvil (2400).

The placement of proximity sensors (2402) relative to anvil (2400), define multiple loading zones (2406). In the present example, the three proximity sensors (2402) define three loading zones (2406) where each loading zone (2406) represents the area or region surrounding and including a respective proximity sensor (2402).

Figure 13B:
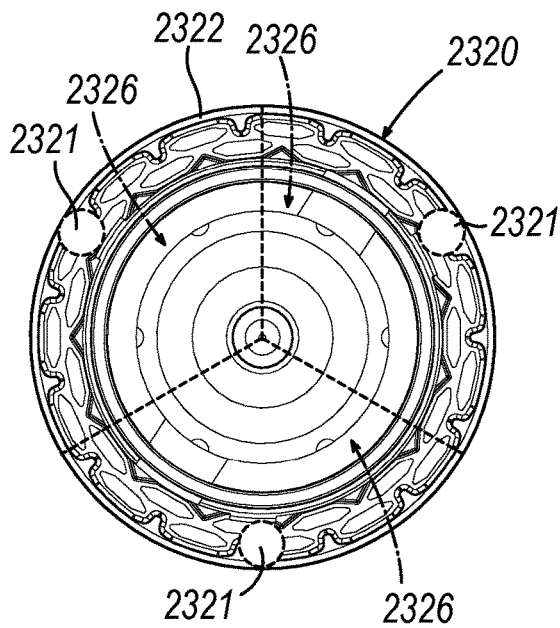
FIG. 13B depicts a top view of an exemplary deck member configured for use with the circular stapler of FIG. 1, with a deck surface having multiple proximity sensors.

FIG. 13B depicts another example where hall effect or proximity sensors are located on the deck member instead of the anvil. In FIG. 13B, an exemplary deck member (2320) is configured for use with instrument (10). For instance, in some versions deck member (2302) replaces deck member (320). With the exception of the features noted below, deck member (2320) is otherwise the same as deck member (320) such that the description herein of deck member (320) applies equally to deck member (2320).

Deck member (2320) is configured with one or more sensors, which in the present example comprise hall effect or proximity sensors (2321). Proximity sensors (2321) are connected with deck surface (2322) of deck member (2320) and are configured to detect and measure the distance between deck surface (2322) and proximal surface (412) of anvil (400) when anvil (400) compresses tissue (12) against deck member (2320). As shown in the present example, three or more sensors or proximity sensors (2321) are used, and in this case three proximity sensors (2321). Additionally, in the present example, proximity sensors (2321) are spaced equally apart from one another. Each proximity sensor (2321) has a pair of wires or conductors that connect with each respective proximity sensor (2321) and are then routed to other components of instrument (10) for signal process as will be discussed further below.

The placement of proximity sensors (2321) relative to deck member (2320), define multiple loading zones (2326). In the present example, the three proximity sensors (2321) define three loading zones (2326) where each loading zone (2326) represents the area or region surrounding and including a respective proximity sensor (2321). In still other versions, either anvil (2400) of FIG. 13A, or deck member (2320) of FIG. 13B can be configured with greater or fewer sensors and loading zones as will be apparent to those skilled in the art in view of the teachings herein.

C. Exemplary Load Cells

Figure 14:
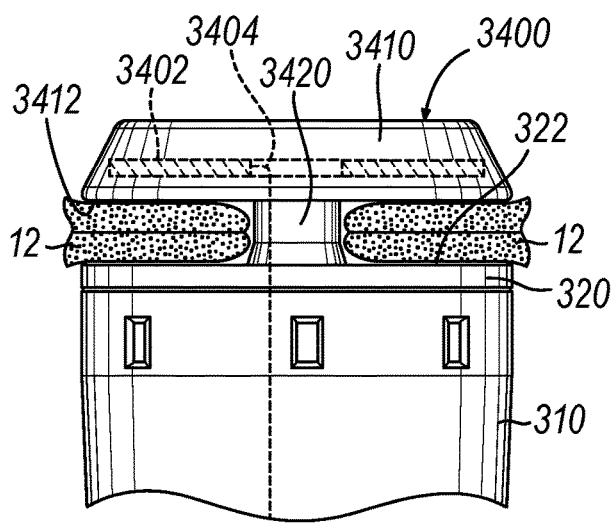
FIG. 14 depicts a side view of an exemplary anvil with load cells shown in phantom and configured for use with the circular stapler of FIG. 1, shown with the stapling head assembly of the circular stapler of FIG. 1.

In other versions of instrument (10), instrument (10) is configured with load cells connected with the anvil or the deck member to aid in the determination of a uniform loading condition. In some versions, load cells may be used instead of the strain gauges and/or proximity sensors discussed above. In other versions, multiple sensor types can be used in combination. FIG. 14 depicts an exemplary anvil (3400) configured for use with instrument (10). For instance, in some versions anvil (3400) replaces anvil (400). With the exception of the features noted below, anvil (3400) is otherwise the same as anvil (400) such that the description herein of anvil (400) applies equally to anvil (3400).

Anvil (3400) is configured with one or more sensors, which in the present example comprise a ring style load cell (3402). In the present example, load cell (3402) is positioned within head (3410) of anvil (3400) and is configured to detect and measure the load imparted on anvil (3400) when anvil (3400) compresses tissue (12) against deck surface (322) of deck member (320). As shown in the present example, load cell (3402) is in a ring configuration surrounding shank (3420). A wire or conductor (3404) connected with load cell (3402) is routed through shank (3420) of anvil (3400) and then routed to other components of instrument (10) for signal process as will be discussed further below.

Load cell (3402) is configured to detect load along multiple circumferential regions or loading zones of load cell (3402). For instance, in one example, load cell (3402) comprises multiple interconnected strain gauges spaced circumferentially within load cell (3402). In such an example, each strain gauge defines a loading zone. For instance, in an example where load cell (3402) comprises four interconnected strain gauges, a loading zone is defined that represents the area or region surrounding and including a respective strain gauge location within load cell (3402). In view of the teachings herein, other ways to configured load cell (3402) and the loading zones thereof will be apparent to those skilled in the art.

Figure 15:
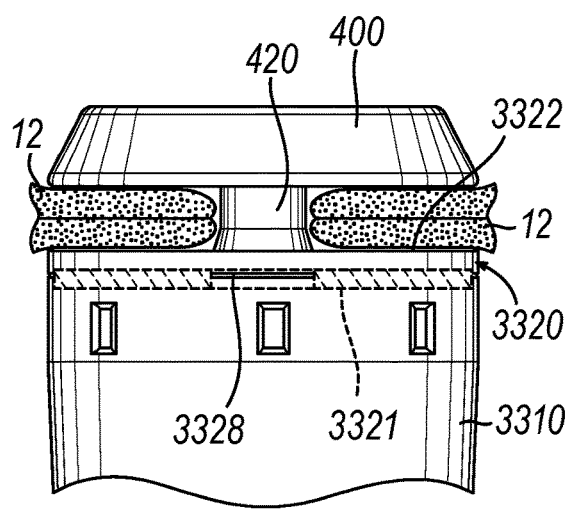
FIG. 15 depicts a side view of an exemplary stapling head assembly with load cells shown in phantom and configured for use with the circular stapler of FIG. 1, shown with the anvil of the circular stapler of FIG. 1.

FIG. 15 depicts an exemplary deck member (3320) configured for use with instrument (10). For instance, in some versions deck member (3320) replaces deck member (320). With the exception of the features noted below, deck member (3320) is otherwise the same as deck member (320) such that the description herein of deck member (320) applies equally to deck member (3320).

Deck member (3320) is configured with one or more sensors, which in the present example comprise a ring style load cell (3321). In the present example, load cell (3321) is positioned beneath a proximal or underside surface (3328) of deck member (3320) and is configured to detect and measure the load imparted on deck member (3320) when anvil (400) compresses tissue (12) against deck surface (3322) of deck member (3320). As shown in the present example, load cell (3321) is in a ring configuration extending circumferentially along proximal surface (3328) opposite deck surface (3322). In the present example, body member (3310) is slightly modified compared to body member (310) described above so that body member (3310) is able to connect with deck member (3320) while also accommodating load cell (3321). A wire or conductor connected with load cell (3321) extends to other components of instrument (10) for signal process as will be discussed further below.

Load cell (3321) is configured to detect load along multiple circumferential regions or loading zones of load cell (3321). For instance, in one example, load cell (3321) comprises multiple interconnected strain gauges spaced circumferentially within load cell (3321). In such an example, each strain gauge defines a loading zone. For instance, in an example where load cell (3321) comprises four interconnected strain gauges, a loading zone is defined that represents the area or region surrounding and including a respective strain gauge location within load cell (3321). In view of the teachings herein, other ways to configured load cell (3321) and the loading zones thereof will be apparent to those skilled in the art.

D. Exemplary Signal Communication

As discussed above, the various load sensing configurations provide ways to measure the load applied to the tissue captured and compressed between the anvil and deck member of the stapling head assembly. Each of the above described sensor configurations produce an output signal that represents the measured quantity. The signal is transmitted from the sensor through instrument (10) to other components for signal processing as will be described further below.

With instrument (10), the anvil is separable from the stapling head assembly as described above with respect to anvil (400). In those versions of instrument (10) where one or more sensors are connected with the anvil, i.e. anvil (1400, 2400, 3400), wires or conductors (1404, 2404, 3404) connect with one or more sensors as described above. Furthermore, wires (1404, 2404, 3404), in their respective configurations described above, extend through or along respective shanks (1420, 2420, 3420) and ultimately attach with contacts (408A, 408B) connected with shank (1420, 2420, 3420). When anvil (1400, 2400, 3400) is reattached with stapling head assembly (300), further contacts and/or wiring within instrument (10) engage with the contacts (408A, 408B) of anvil (1400, 2400, 3400) to establish an electrical communication pathway for the signals output from the one or more sensors.

FIG. 16A depicts an exemplary electrical contact configuration for an anvil incorporating sensors as described above. In the present example of FIG. 16A, the anvil may represent anvil (1400) with strain gauges (1402), anvil (2400) with proximity sensors (2402), or anvil (3400) with load cell (3402). In this manner, anvils (1400, 2400, 3400) are shown with respective wires (1404, 2404, 3404) extending through respective shanks (1420, 2420, 3420) and ultimately attaching with contacts (408A). Contacts (408A) in the example of FIG. 16A are located inside shank (1420, 2420, 3420) of anvil (1400, 2400, 3400) at a proximal end.

In one example of anvil (1400), wires (1404) from each respective strain gauge (1402) connect to a respective one of contacts (408A). In one example of anvil (2400), wires (2404) from each respective hall effector or proximity sensor (2402) connect to a respective one of contacts (408A). In one example of anvil (3400), wire (3404) from load cell (3402) connects to contact (408A). In other versions for anvils (1400, 2400, 3400) there may be greater or fewer contacts (408A) such that each of contacts (408A) may connect with, or be associated with, more than one sensor via one or more of the wires. In view of the teachings herein, other configurations for establishing electrical communication between the one or more sensors and the one or more contacts will be apparent to those skilled in the art.

As shown in FIG. 16A, contacts (408A) are in the form of a ring or circular structure that extends along the inner surface of shank (1420, 2420, 3420). In this manner, contacts (408A) have a 360 degree area of contact such that when each respective anvil (1400, 2400, 3400) is connected with stapling head assembly (300) contacts (408A) will make an electrical connection with corresponding contacts or electrical features within stapling head assembly (300) regardless of the rotational orientation of anvil (1400, 2400, 3400) at the time anvil (1400, 2400, 3400) attaches with stapling head assembly (300).

FIG. 16B depicts another exemplary electrical contact configuration for an anvil incorporating sensors as described above. In the present example of FIG. 16B, the anvil may represent anvil (1400) with strain gauges (1402), anvil (2400) with proximity sensors (2402), or anvil (3400) with load cell (3402). In this manner, anvils (1400, 2400, 3400) are shown with respective wires (1404, 2404, 3404) extending along respective shanks (1420, 2420, 3420) and ultimately attaching with respective contacts (408B). As shown in FIG. 16B, contacts (408B) in the present example are integrated into alignment tabs (426) of shanks (1420, 2420, 3420) of anvils (1400, 2400, 3400).

In one example of anvil (1400), wires (1404) from each respective strain gauge (1402) connect to a respective one of contacts (408B). In one example of anvil (2400), wires (2404) from each respective hall effector or proximity sensor (2402) connect to a respective one of contacts (408B). In one example of anvil (3400), wire (3404) from load cell (3402) connects to contact (408B). In other versions for anvils (1400, 2400, 3400) there may be greater or fewer contacts (408B) such that each of contacts (408B) may connected with, or be associated with, more than one sensor via one or more of the wires. In view of the teachings herein, other configurations for establishing electrical communication between the one or more sensors and the one or more contacts will be apparent to those skilled in the art.

As shown in FIG. 16B, contacts (408B) are integrated into alignment tabs (426), and such alignment tabs (426) are circumferentially spaced about shank (1420, 2420, 3420). In this manner, contacts (408B) have multiple areas of contact that are spaced about the longitudinal axis of shank (1420, 2420, 3420) such that when each respective anvil (1400, 2400, 3400) is connected with stapling head assembly (300), contacts (408B) will make an electrical connection with corresponding contacts or electrical features within stapling head assembly (300) regardless of the rotational orientation of anvil (1400, 2400, 3400) at the time anvil (1400, 2400, 3400) attaches with stapling head assembly (300).

In some versions of instrument (10) described above, the one or more sensors were associated with deck member (2320, 3320) rather than the anvil. In these versions of instrument (10), the signal output from the one or more sensors originates within components of stapling head assembly (300). As such, the electrical contacts configurations for the anvils shown in FIGS. 16A and 16B may be omitted in these versions.

Figure 17:
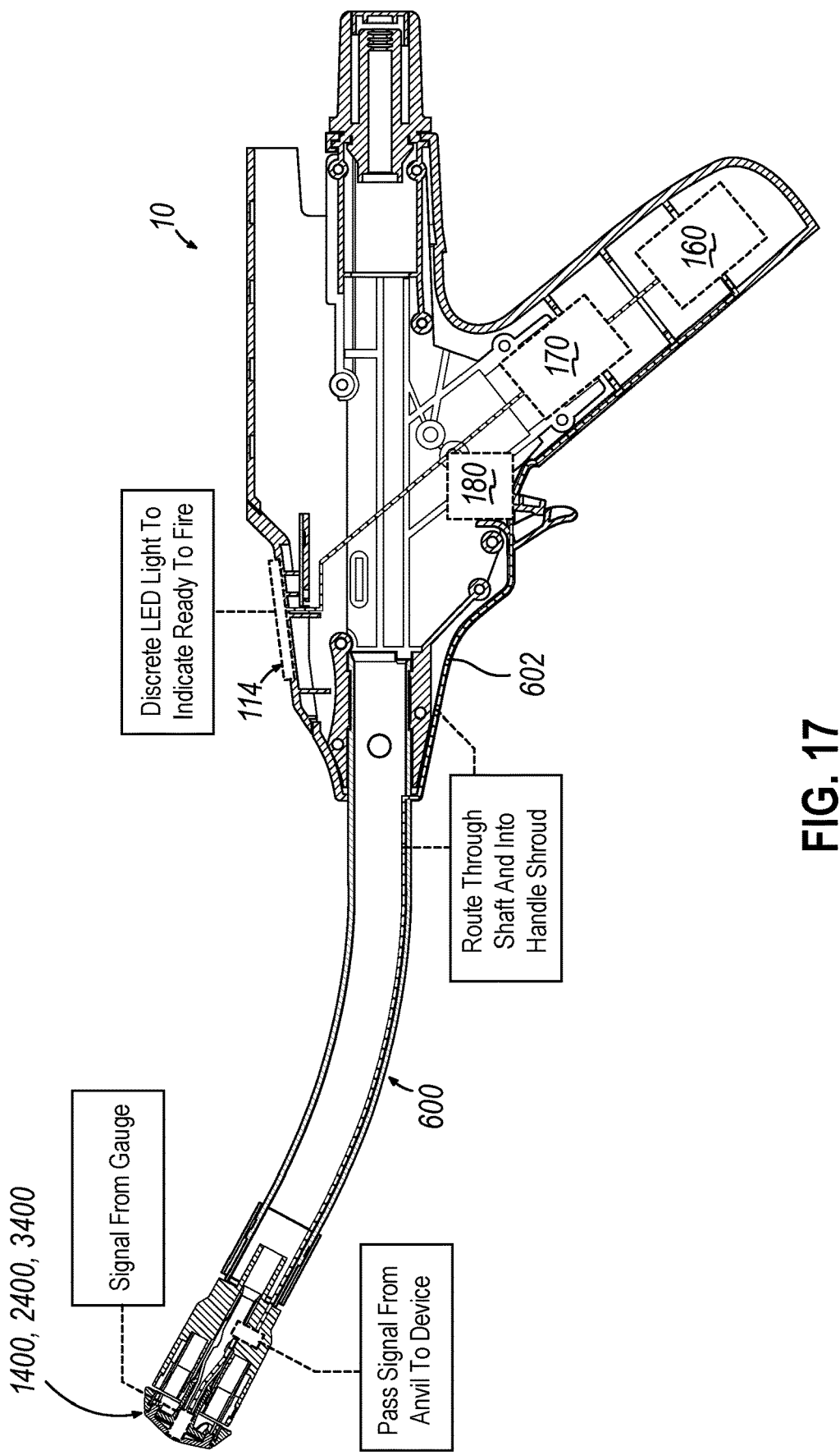
FIG. 17 depicts a side view in cross-section of the surgical stapler of FIG. 1, showing an electrical pathway for communicating signals from sensors within the anvil.

FIG. 17 depicts a cross-section view of instrument (10), and in particular an exemplary signal pathway (600) from the anvil through the remainder of instrument (10). As mentioned above, the one or more sensors generate an output signal indicative of the measured parameter such as force, load, position, distance, gap, or deflection, etc. If the output signal originated in one or more sensors within the anvil, then a first part of signal pathway (600) is to pass the signal from the anvil to the remainder of instrument (10) by using a configuration for the anvil that incorporates an electrical contact configuration, such as those configurations shown and described above with respect to FIGS. 16A and 16B. If the output signal originated in one or more sensors within the deck member, then it is not necessary to pass the signal from the anvil to stapling head assembly (300).

With the signal within stapling head assembly (300), a second part of signal pathway (600) is routing the signal through shaft assembly (200) and into body or handle assembly (100). In one version, one or more wires or conductors (602) are used to transmit the signals from the one or more sensors through instrument (10). For instance, wire (602) extends continuously from shaft head assembly (300), through shaft assembly (200), and in into handle assembly (100). Within handle assembly (100), wire (602) connects with a control module (170). Control module (170) is configured to receive and process the signals from the one or more sensors. In this respect, control module (170) can include a printed circuit board (PCB) with a processor or programmable logic device (PLD) thereon to process the signals or apply various logic arrays to the signals. After processing, a third part of signal pathway (600) is routing the output from control module (170) to user interface (114) to display a result to a user. Wire (602) or another wire can be used to route this output in this manner.

While the above examples describe a hardwired signal routing approach, to other components of instrument (10), in other versions the captured signals from the one or more sensors used to detect and measure load uniformity can be routed to other processor devices outside or separate from instrument (10) itself. Additionally, in some other versions, signals may be transmitted within components of instrument (10), or to devices outside of instrument (10), using wireless communication features. In view of the teachings herein, these and various other ways to route signals from the one or more sensors will be apparent to those skilled in the art.

E. Exemplary Signal Processing and Outputs

Control module (170) is configured to control instrument (10) based on the results or output from the applied logic arrays or signal processing. For instance, in one example where the signals indicate that a uniform tissue load condition is achieved, control module (170) may illuminate an indicator (508), such as an LED light, on user interface (114) to communicate to a user that it is acceptable to fire instrument (10), or that instrument (10) is ready to fire. Where non-uniform load exists, control module (170), after processing the signals, may illuminate a different indicator (516) on user interface (114) to communicate to a user that instrument (10) is not ready for firing. Still in other versions, control module (170) can be configured to lock or prevent the ability to fire instrument (10) rather than just provide an indication on user interface (114). For instance, where a non-uniform or uneven loading is detected, control module (170) may prevent motor activation module (180) from activating motor (160) thereby preventing firing of instrument (10). In view of the teachings herein, other ways to configure signal pathway (600), including control module (170), will be apparent to those skilled in the art.

In some versions, one of indicators (508, 516) may be omitted and control module (170) is configured to illuminate the remaining indicator with a different color LED based on the condition of the load and its uniformity. For instance, a green LED may be used where there is uniform loading detected, indicating instrument (10) is ready to fire. Similarly, a red or yellow LED may be used where there is non-uniform loading detected, indicating instrument (10) is not ready to fire. Still in other examples, color-coded indication can be replaced with textual phrases that illuminate based on the condition detected. For instance, phrases like "Ready to Fire," "Pass," "Fail," etc. can be incorporated into one or more indicators (508, 516). Similarly, symbols may be used as the indication, e.g., an "X" when not ready to fire, and a check-mark symbol when ready to fire. In view of the teachings herein, other ways to indicate to a user the status of the loading condition as well as whether instrument (10) is ready to fire will be apparent to those skilled in the art.

In some versions instrument (10) is configured for manual firing by the user. In these instances, the indication provided regarding the uniformity of the loading at user interface (114) informs the user so the user can determine if a firing action should be completed. In some other versions instrument (10) is configured for automated firing. In such instances, the determination of the condition of uniform loading is incorporated into the firing algorithm such that firing may not occur unless and until the uniform loading condition is achieved. In some cases, an option may be provided to override the requirement for uniform loading prior to firing instrument (10).

As mentioned above, control module (170) uses various logic arrays in processing the signals received by control module (170). For example, in one version where instrument (10) is used with anvil (1400) having strain gauges (1402), a predetermined threshold may be defined that represents an acceptable deviation from a median strain measured across all strain gauges (1402). Where any one of strain gauges (1402) measures a strain outside this predetermined threshold of strain deviation from the median, control module (170) would output a result indicating that uniform loading has not been achieved, or in other words that there is an uneven or non-uniform load applied to the tissue between the anvil and deck member. Similar logic arrays are used in some version where load cells (3402, 3321) are used with instrument (10) instead of, or in addition to strain gauges (1402).

In another example where instrument (10) uses hall effect or proximity sensors (2402) to measure differences in the gap between the underside or proximal anvil surface and the deck surface, the logic array is configured with a predetermined threshold for acceptable deviation from a median distance or gap as measured by the proximity sensors (2402). For instance, if one of sensor (2402) indicates a distance or gap that exceeds this predetermined threshold, then control module (170) would output a result indicating that uniform loading has not been achieved, or in other words that there is an uneven or non-uniform load applied to the tissue between the anvil and deck member. In view of the teachings herein, other ways to establish predetermined thresholds for use with the one or more sensors described above and various logic arrays to assess the uniformity of the load applied to the compressed tissue will be apparent to those skilled in the art in view of the teachings herein. By way of example only, and not limitation, in some other versions, a preset limit regarding uniformity of load may be established based upon a difference between the largest reading and smallest reading from the multiple sensors.

III. Exemplary Methods of Use

A. Use of Surgical Stapler with Uniform Load Detection

Figure 18:
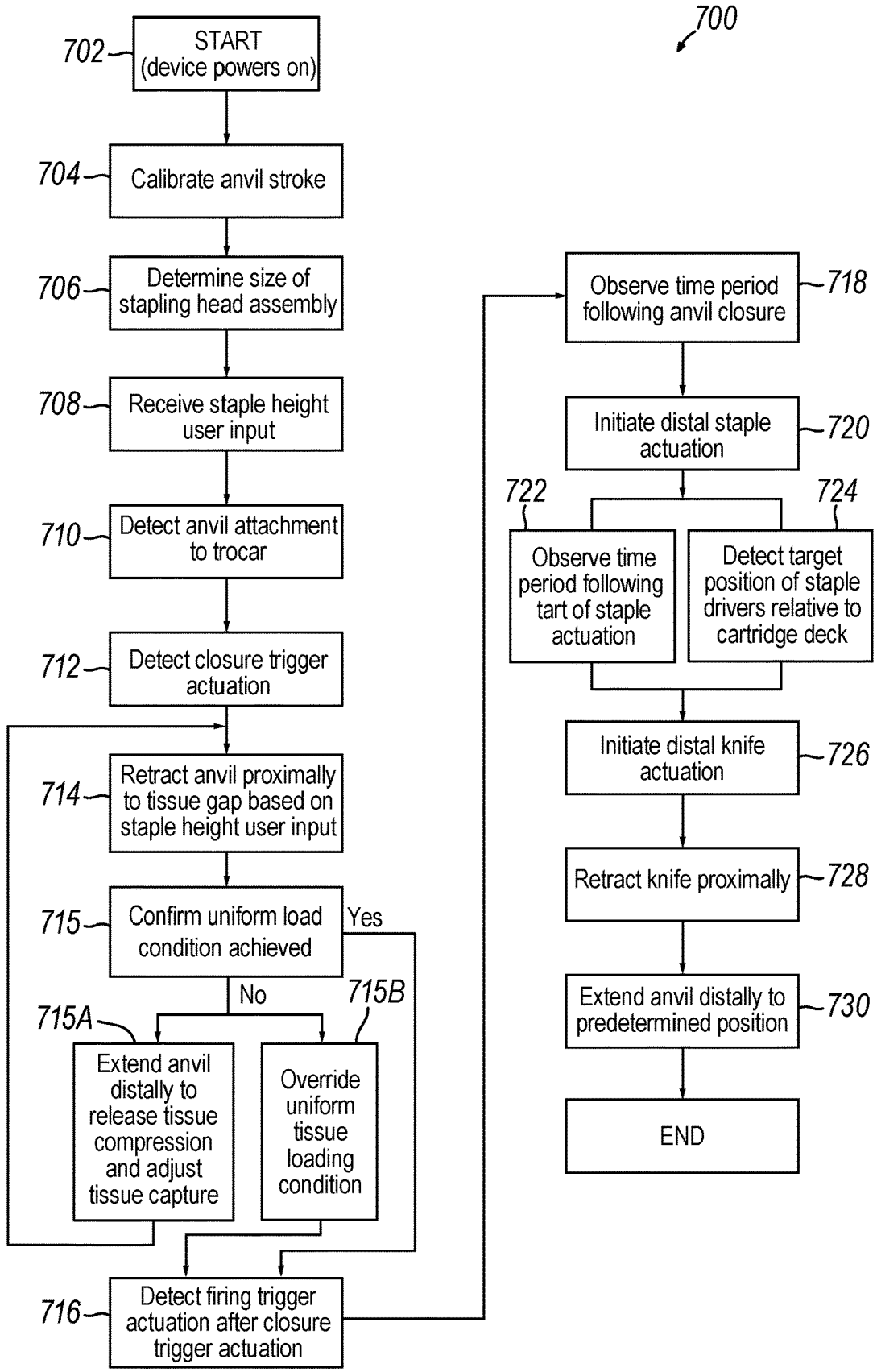
FIG. 18 depicts a block diagram of an exemplary method of using the surgical stapler of FIG. 1 having one or more sensors for determining tissue loading uniformity.

FIG. 18 shows an exemplary method (700) for controlling circular surgical stapling instrument (10) configured with the tissue loading sensing for uniform loading detection. At step (702), instrument (10) powers on in response to being energized by battery pack (120), for example when battery pack (120) is fully inserted into the proximal end of handle assembly (100) after instrument (10) is removed from product packaging. Upon removal from the packaging, one of anvils (400, 1400, 2400, 3400) is already secured to trocar (330) and is in a fully open state. Similarly, one of deck members (320, 2320, 3320) is connected with stapling head assembly (300) depending on the configuration of instrument (10) being used.

After instrument (10) powers on in the present example, control module (170) enters an anvil stroke calibration mode at step (704), which may occur automatically or in response to a user input, for example provided via user interface (114). In this calibration mode, control module (170) activates motor activation module (180) to retract trocar (330) proximally and thereby close anvil (400, 1400, 2400, 3400) against deck surface (322, 2322, 3322) after a staple retainer has been removed. Control module (170) may detect that anvil (400, 1400, 2400, 3400) has reached a closed position by detecting via a sensor an increase in the electrical current load of motor (160) upon contact of anvil (400, 1400, 2400, 3400) with deck surface (322, 2322, 3322). Control module (170) observes the stroke (i.e., longitudinal displacement) of anvil (400, 1400, 2400, 3400) during this retraction process and compares it to an expected stroke of anvil (400, 1400, 2400, 3400). Based on this comparison and any differences observed between the two stroke values, control module (170) then calibrates an actuation algorithm that is executed to activate motor activation module (180) to actuate trocar (330) and thereby ensure precise actuations of anvil (400, 1400, 2400, 3400) thereafter during a surgical procedure. In addition, or in the alternative, calibration of the anvil stroke may be performed by control module (170) in real time during a surgical procedure when anvil (400, 1400, 2400, 3400) is being retracted to clamp tissue. It will be understood that the strokes of one or more other actuatable members of instrument (10) may be calibrated in a similar manner before or during a surgical procedure, and also that the calibration of the anvil closure stroke may be applied by control module (170) to also calibrate the stapling stroke and/or the cutting stroke of instrument (10).

At step (706), control module (170) determines a diameter of stapling head assembly (300). As described above, stapling head assembly (300) may be releasably attached to shaft assembly (200) such that stapling head assemblies (300) of various diameters may be interchangeably coupled with the distal end of shaft assembly (200) depending on a lumen size of the tissue structure being operated on with instrument (10). Control module (170) is configured to make this size determination based on user input provided via user interface (114) and/or information provided by a sensor, for instance when a sensor is configured to detect the size of stapling head assembly (300).

At step (708), control module (170) receives from user interface (114) input that indicates a desired height of staples to be formed in tissue, as selected by the operator via user interface (114). Control module (170) equates this staple height to a corresponding gap distance (d) (see FIG. 7C) to be established between anvil (400, 1400, 2400, 3400) and deck surface (322, 2322, 3322) of stapling head assembly (300) at a closed position of anvil (400, 1400, 2400, 3400), in order to achieve the selected staple height.

While steps (704, 706, 708) are shown in FIG. 18 as being performed in a particular order, it will be appreciated that these steps (704, 706, 708) may be performed in a variety of orders relative to one another following the powering on of instrument (10) in step (702) and before the actuation or firing of instrument (10).

Following completion of steps (704, 706, 708), the operator detaches anvil (400, 1400, 2400, 3400) from trocar (330) and proceeds to position anvil (400, 1400, 2400, 3400) within a first tubular tissue structure of a patient and separately position stapling head assembly (300) within a second tubular tissue structure of the patient. The operator then attaches anvil (400, 1400, 2400, 3400) to trocar (330) within the patient, for example as shown in FIGS. 7A-7B described above, at which point control module (170) detects at step (710) that the attachment has been made. Such detection may be made by a sensor, which communicates a corresponding signal to control module (170).

At step (712), control module (170) detects that safety trigger (140) has been actuated by the operator. Control module (170) then proceeds to step (714) and directs motor activation module (180) to actuate trocar (330) proximally and thereby retract anvil (400, 1400, 2400, 3400) to a closed position at which the selected staple height and corresponding gap distance (d) are achieved. In some versions, control module (170) may be configured to initiate retraction of trocar (330) and anvil (400, 1400, 2400, 3400) only in response to an actuation of safety trigger (140) that occurs after attachment of anvil (400, 1400, 2400, 3400) to trocar (330) has been detected at step (710). The operator may monitor the retraction of anvil (400, 1400, 2400, 3400) toward its closed position via visual indicia and/or displayed graphics of user interface (114).

Additionally, in some versions, control module (170) may control motor activation module (180) to retract anvil (400, 1400, 2400, 3400) proximally through the anvil closure stroke in two sequential stages. For instance, control module (170) may direct motor activation module (180) to retract anvil (400, 1400, 2400, 3400) through a first portion of the anvil closure stroke, at which point control module (170) pauses activation of motor activation module (180) for a predetermined period of time (e.g., several seconds). At the end of this wait period, control module (170) reactivates motor activation module (180) to continue retracting anvil (400, 1400, 2400, 3400) through the remaining portion of the anvil closure stroke to its closed position. Inclusion of such a pause in the retraction of anvil (400, 1400, 2400, 3400) may enable the tissue being compressed between anvil (400, 1400, 2400, 3400) and deck surface (322, 2322, 3322) to at least partially settle (or "creep"). Advantageously, this settling of tissue yields a reduction of the axial extension load on trocar (330) and the resulting electrical current load of motor (160) as anvil (400, 1400, 2400, 3400) advances proximally to its fully closed position defined by the target staple height input provided by the user in step (708).

At step (715), control module (170) receives signals from the one or more sensors (1402, 2402, 2321, 3402, 3321) from either anvil (400, 1400, 2400, 3400) or deck member (322, 2322, 3322) based on the configuration of instrument (10) being used. As discussed above, signals travel along signal pathway (600) via wire (602) and are received at control module (170) for processing. Based on the processing rules and logic arrays described above, control module (170) sends an output result to user interface (114) in the form of an indicator (508, 516) to communicate and confirm with the operator whether a uniform tissue loading has been achieved. Again, the uniformity determination is made in accordance with the predetermined thresholds and values that are inputs to the logic arrays used when processing the signals. Where indicator (508, 516) displays an uneven or non-uniform tissue loading, in some versions, upon confirmation from the operator, i.e. by an input received via user interface (114), actuating safety trigger (140) again, or via another way, anvil (400, 1400, 2400, 3400) is extended distally to relieve the tissue compression or load such that tissue capture is adjusted or attempted again as shown at step (715A). Thereafter, anvil (400, 1400, 2400, 3400) is retracted proximally again to re-attempt tissue capture and compression to achieve uniform loading. Note that such operator confirmation is not required in all versions. Where indicator (508, 5616) displays that the compressive load on the tissue is within the preset limits such that a condition of uniform loading is achieved, method (700) proceeds as described below. As shown in step (715B), in some versions the method (700) can proceed as described below even with uneven or non-uniform tissue loading. For instance, an operator can override the non-uniform loading condition check or requirement in some versions to proceed with the stapling action despite the presence of a non-uniform tissue loading condition. By way of example only, and not limitation, such an overriding action can occur by receiving an input from the operator via user interface (114), actuation of safety trigger (140) in a prescribed override sequence, or via another way as will be apparent to those of ordinary skill in the art in view of the teachings herein.

At step (716), control module (170) detects that firing trigger (150) has been actuated by the operator following completion of the anvil closure stroke. Note that in some versions, firing trigger (150) may be locked out or unable to be actuated where non-uniform tissue loading is indicated according to control module (170) as mentioned above. This is not required in all version, but in those versions where used, it prevents firing instrument (10) inadvertently where a condition of uneven tissue loading exists. In the present example with a uniform tissue loading condition, in response to detecting this actuation of firing trigger (150), control module (170) observes completion of a predetermined period of time measured from completion of the anvil closure stroke, during which staple drive member (350) and knife member (340) remain stationary. This wait period after anvil closure enables the clamped tissue to settle (or "creep") into its fully compressed state before stapling head assembly (300) is fired, thus reducing the axial loads on staple drive member (350) and knife member (340), and the resulting current loads of motor (160), during the respective stapling and cutting sequences. It will be understood that this wait period may be omitted in some versions.

Upon completion of the wait period denoted in step (718), control module (170) initiates distal actuation of staple driver member (350) at step (720) to begin stapling the clamped tissue. In particular, control module (170) activates motor activation module (180) to engage and drive staple drive member (350) to actuate staple driver member (350) distally through stapling head assembly (300) and thereby drive staples into tissue (12) and against anvil (400, 1400, 2400, 3400), for example similar to the manner shown in FIG. 7D. Upon actuation of staple drive member (350), control module (170) at step (722) observes another predetermined period of time during which motor (160) continues to drive staple drive member (350) through the stapling stroke. Simultaneously, at step (724) control module (170) communicates with a sensor to detect when staple driver member (350) reaches a predetermined longitudinal position within stapling head assembly (300). Such a position may correspond to the point at which individual staple drivers (352) reach deck surface (322, 2322, 3332) such that the staples are at least partially formed within the clamped tissue (12). This process is described in further detail in U.S. patent application Ser. No. 16/574,797, entitled "Method for Controlling Cutting Member Actuation for Powered Surgical Stapler," filed on Sep. 18, 2019, the disclosure of which is incorporated by reference herein.

In response to detecting completion of the predetermined time period of step (722) and/or detecting at step (724) that staple driver member (350) has reached the predetermined longitudinal position, control module (170) then initiates distal actuation of the knife member (340) at step (726) to begin cutting the tissue (12). In particular, control module (170) activates motor activation module (180) to engage and drive knife member (340) distally through stapling head assembly (300) and thereby cut the tissue, for example similar to the manner shown in FIG. 7D.

As noted above, delaying initiation of the cutting stroke relative to initiation of the stapling stroke, as enabled by independent actuation of staple drive member (350) and knife member (340), ensures at least partial formation of staples within the tissue before tissue cutting commences. Advantageously, this approach enables the staples to anchor within the clamped tissue before cutting, and thereby prevent lateral shifting of the tissue and resulting malformation of the staples when the knife member is driven distally. Of course, in other versions the stapling and cutting can occur substantially simultaneously such that independent actuation of staple driver member (350) and knife member (340) is not required in all versions of method (700).

The end of the distal cutting stroke of knife member (340) may correspond to a point at which knife member (340) breaks washer (417) within anvil (400, 1400, 2400, 3400). Upon completion of the distal cutting stroke, control module (170) at step (728) directs motor activation module (180) to retract knife member (340) proximally back into stapling head assembly (300). In some versions, knife member (340) distal extension and subsequent proximal retraction may be achieved by powering motor (160) through a continuous, uniform range of motion, for example as disclosed in U.S. Pub. No. 2017/0258471 incorporated by reference above. In other versions, control module (170) may be programmed to communicate with a sensor to detect completion of the distal cutting stroke, and thereafter specifically direct motor activation module (180) to drive knife member (340) to retract knife member (340) proximally. In any of such versions, the sensor may comprise an encoder configured to monitor a rotational output of motor (160).

Simultaneously with or subsequently to knife retraction step (728), control module (170) at step (730) directs motor activation module (180) to drive trocar (330) distally to thereby extend anvil (400, 1400, 2400, 3400) distally to a predetermined position relative to deck surface (322, 2322, 3322) of stapling head assembly (300). This distal extension enables the stapled tissue to be released from between anvil (400, 1400, 2400, 3400) and stapling head assembly (300) so that instrument (10) may be withdrawn from the patient while anvil (400, 1400, 2400, 3400) remains attached to trocar (330).

B. Determining Uniform Tissue Loading Condition

Figure 19:
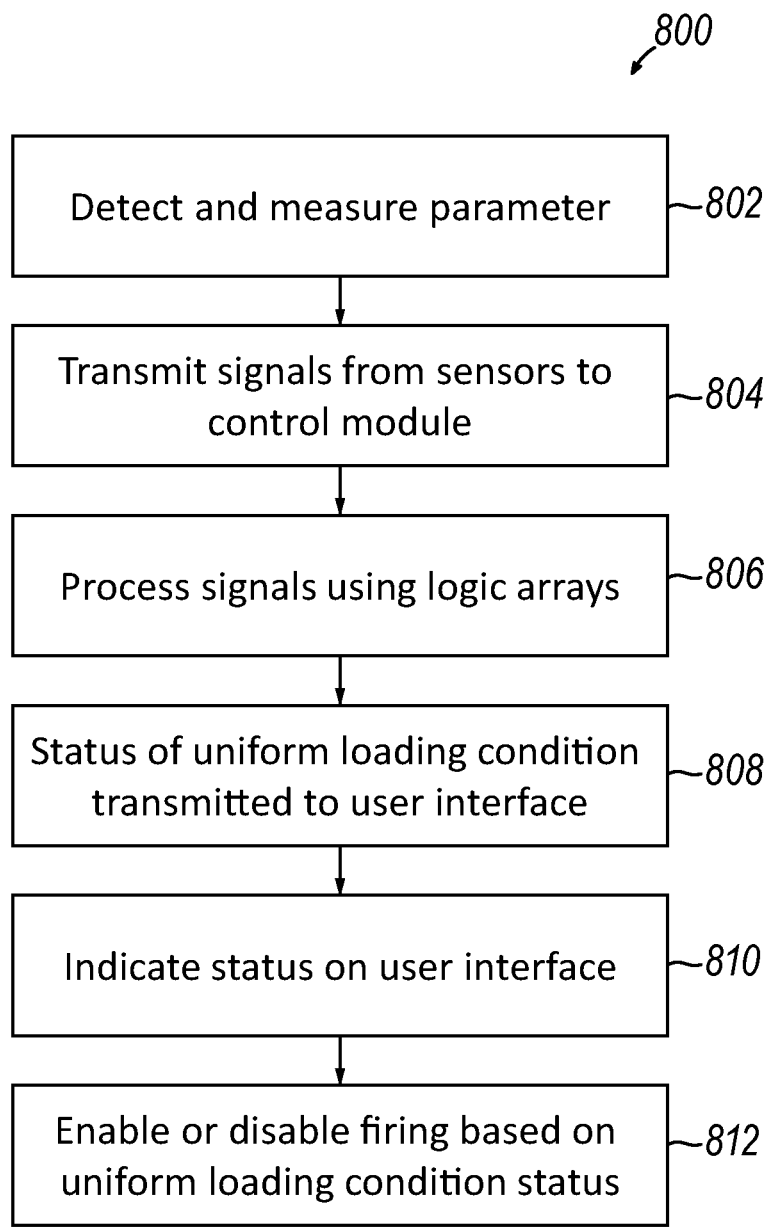
FIG. 19 depicts a block diagram of an exemplary method of determining whether a uniform tissue loading condition has been achieved.

FIG. 19 depicts a block diagram of method (800) for determining when a uniform tissue loading condition is achieved. In the absence of a uniform tissue loading condition, method (800) is further usable for determining when an uneven or non-uniform tissue loading condition exists. At step (802), a parameter is detected and measured by one or more sensors (1402, 2402, 2321, 3321, 3402). As mentioned above, in some versions, the parameter detected is strain, load, and/or position or gap. Moreover, the parameters detected are usable to assess, directly or indirectly, the uniformity of the load on the tissue compressed between the anvil and deck surface of stapling head assembly (300).

At step (804), a signal associated with the measured parameter is transmitted from the one or more sensors (1402, 2402, 2321, 3321, 3402) to control module (170) of instrument (10). Then at step (806), at control module (170), the input signals are processed by applying one or more logic arrays to determine whether a uniform load condition is satisfied. Within processing step (806), a comparison is made comparing the parameters detected and measured to a preset limit or threshold defined and incorporated into the logic arrays. For example, the present limit may be an explained above where the measured parameter of strain at each strain gauge (1402) cannot deviate from the median strain by more than a predetermined amount or percentage.

By way of example only, and not limitation, in some versions the acceptable deviation from the median value is +/−10%. Of course, in other versions this amount of acceptable deviation from the median may be greater or less than 10%. As described above, other metrics and preset limits may be used with the logic arrays to determine whether a uniform tissue loading condition has been achieved.

At step (808), a status of the uniform load condition from step (806) is transmitted to user interface (114) of instrument (10). At step (810), that status is indicated on user interface (114), for example as described above with respect to indicators (508, 516). In some versions, where an automated firing system is used, certain indication steps may be omitted as this output is built into the firing algorithm. Of course, in some versions these indication steps can still be used even with an automated firing system. In some versions of method (800), after step (810), step (812) enables or disables firing of instrument (10) based on the status of the uniform tissue loading condition from step (808). In some versions, step (812) may be omitted and the indication of step (810) is informational for the operator who can then decide upon firing instrument (10) or attempting to recapture tissue based on a non-uniform load status indication. As mentioned above, in some versions of instrument (10) where firing may be disabled based on the determination of uniform tissue loading, the operator can have an option to override this disabling such that instrument (10) can be fired even where uneven tissue loading is present. This overriding ability though is not required in all versions.

It should be noted that with method (800), the steps shown may be performed in sequences other than that shown. It should further be understood that one or more of the steps may be omitted. Also, it should be understood that these steps are not exhaustive and that additional steps may be included in other versions of method (800). In view of the teachings herein, various modifications to method (800) will be apparent to those skilled in the art.

C. Tracking Loading and Performance and/or Patient Outcomes

In addition to using instrument (10) with its uniform load sensing features to determine or verify a uniform load condition or state prior to firing instrument (10), in other instances certain performance metrics can be established and tracked based upon the load sensing data. For instance, in one example, the signals detected by the one or more sensors for measuring loading uniformity can be processed and stored to create a history documenting the degree of loading uniformity achieved when using instrument (10). With this data, comparisons can be made to assess a given instrument's performance over time, or the performance of one instrument compared to another. In certain cases, where a given instrument is underperforming in its ability to consistently achieve a uniform loading profile for the tissue captured and compressed between the anvil and deck, that instrument can be serviced to improve its performance or otherwise removed from service altogether. Either of these approaches would provide an enhanced ability to reduce or avoid defects in terms of things like incomplete washer cuts and/or malformed staples.

In another example, the signals detected by the one or more sensors for measuring loading uniformity can be processed and stored to create a history documenting the degree of loading uniformity achieved when using instrument (10). Additionally, specific conditions achieved for a given patient can be documented within this history. Accordingly, comparisons can be made examining patient outcomes versus device performance based on load uniformity as measured at the time of instrument's (10) use. With this information, further refinement of acceptable ranges for uniform loading can be determined. This information may in turn be used to revise or update certain predetermined limits or thresholds for using instrument (10).

This information concerning the status or degree of uniform loading achieved during a procedure can be transmitted from instrument (10) to a remote database location on a network by way of a hardwired connection or by wireless communication features. In view of the teachings herein, various ways to capture, transmit, and store data related to the condition of uniform tissue loading at the time of instrument's (10) use will be apparent to those skilled in the art.

Figure 20:
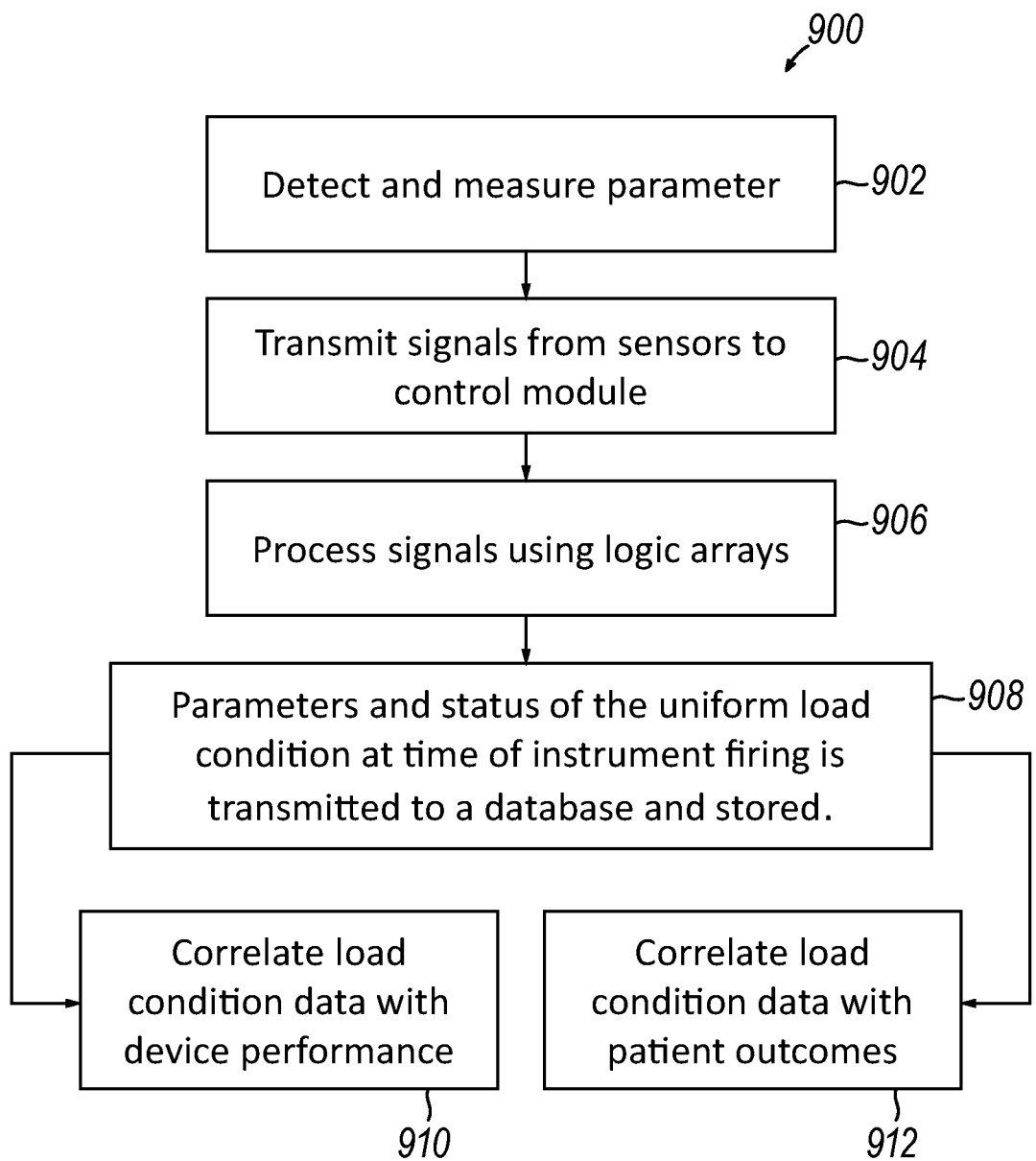
FIG. 20 depicts a block diagram of an exemplary method of tracking and correlating tissue loading uniformity with surgical stapler performance and/or procedure patient outcomes.

By way of example only, FIG. 20 depicts a block diagram of a method (900) for tracking and correlating uniform tissue loading information with either or both of device performance and patient outcomes. With method (900), at step (902) a parameter is detected and measured by one or more sensors (1402, 2402, 2321, 3321, 3402). As mentioned above, in some versions, the parameter detected is strain, load, and/or position or gap. Moreover, the parameters detected are usable to assess, directly or indirectly, the uniformity of the load on the tissue compressed between the anvil and deck surface of stapling head assembly (300).

At step (904), a signal associated with the measured parameter is transmitted from the one or more sensors (1402, 2402, 2321, 3321, 3402) to control module (170) of instrument (10). Then at step (906), at control module (170), the input signals are processed by applying one or more logic arrays to determine whether a uniform load condition is satisfied. Upon or after instrument (10) is fired, at step (908) the measured parameters and the status of the uniform load condition determination is transmitted to a database and stored.

At step (910), the data recorded at step (908) is correlated to performance of instrument (10). In one example this performance is assessed based on how often instrument (10) is able to achieve a uniform tissue loading historically over time compared to itself. Still yet, in another example the performance is assessed based on how often instrument (10) is able to achieve a uniform tissue loading historically over time compared to other similar instruments.

At step (912), the data recorded at step (908) is correlated to the outcomes from patients for which instrument (10) was used. In this manner, the precise usage of instrument (10) is associated with the precise patient and procedure in which instrument (10) was used. In this manner, the data can be analyzed to identify the conditions of use for instrument (10), and its status regarding the condition of tissue loading, that correlate with positive or successful outcomes for patients.

It should be noted that with method (900), the steps shown may be performed in sequences other than that shown. It should further be understood that one or more of the steps may be omitted. Also, it should be understood that these steps are not exhaustive and that additional steps may be included in other versions of method (900). In view of the teachings herein, various modifications to method (900) will be apparent to those skilled in the art.

IV. EXEMPLARY COMBINATIONS

The following examples relate to various non-exhaustive ways in which the teachings herein may be combined or applied. The following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument comprises (a) a body assembly with a proximal end and a distal end; (b) a shaft assembly that extends distally from the distal end of the body assembly and comprises a proximal end and a distal end; (c) a stapling head assembly disposed at the distal end of the shaft assembly, wherein the stapling head assembly is operable to drive a plurality of staples into tissue, wherein the stapling head assembly comprises an anvil-driving shaft configured to selectively move between a distal position and a proximal position within the shaft assembly; (d) an anvil, selectively coupleable with the anvil-driving shaft, wherein the anvil is configured to move between the distal position and the proximal position when coupled with the anvil-driving shaft, wherein the anvil comprises one or more sensors each configured to detect a parameter indicative of tissue loading between the anvil and the stapling head assembly, wherein collectively the parameters detected are indicative of whether the tissue captured between the anvil and the stapling head assembly is subject to a uniform load or a non-uniform load; and (e) a firing member configured to drive movement of the stapling head assembly to drive the plurality of staples into the tissue.

Example 2

The surgical instrument of Example 1, wherein the one or more sensors comprise three or more sensors.

Example 3

The surgical instrument of any one or more of Examples 1 through Example 2, wherein the sensors are located along the circumference of the anvil to define multiple loading zones.

Example 4

The surgical instrument of any one or more of Example 1 through Example 3, wherein each of the sensors are associated with a respective loading zone, and wherein the parameter detected by each respective sensor is associated with the respective loading zone.

Example 5

The surgical instrument of any one or more of Examples 1 through Example 4, wherein the one or more sensors comprise one or more strain gauges.

Example 6

The surgical instrument of Example 5, wherein the parameter detected by the one or more strain gauges comprises a strain experienced by the anvil during tissue compression.

Example 7

The surgical instrument of any one or more of Examples 1 through Example 4, wherein the one or more sensors comprise one or more proximity sensors.

Example 8

The surgical instrument of Example 7, wherein the parameter detected by the one or more proximity sensors comprises a distance between the anvil and a deck surface of the stapling head assembly during tissue compression.

Example 9

The surgical instrument of any one or more of Examples 1 through Example 4, wherein the one or more sensors comprise one or more load cells.

Example 10

The surgical instrument of Example 9, wherein the parameter detected by the one or more load cells comprise a force applied to the tissue during tissue compression.

Example 11

The surgical instrument of any one or more of Examples 1 through Example 11, wherein the one or more sensors are in electrical communication with a processor, and wherein one or more signals from the one or more sensors are communicated to the processor, wherein the one or more signals are associated with the parameter detected by the one or more sensors.

Example 12

The surgical instrument of Example 11, wherein the processor is configured to compare the one or more signals to determine whether the parameter detected by each of the one or more sensors is within a predetermined threshold.

Example 13

The surgical instrument of Example 12, wherein the predetermined threshold comprises a deviation from a median of the parameter detected by each of the one or more sensors.

Example 14

The surgical instrument of any one or more of Examples 1 through Example 13, wherein the anvil further comprises one or more electrical contacts configured to transmit one or more signals from the one or more sensors from the anvil to a conductor extending through stapling head assembly and shaft assembly to body assembly.

Example 15

The surgical instrument of any one or more of Example 1 through Example 14, wherein the body assembly comprises a processor configured to process the one or more signals to generate an output, wherein the output is displayed on a user interface of the body assembly.

Example 16

The surgical instrument of Example 15, wherein the output comprises an indication of whether the load on the tissue compressed between the anvil and a deck surface of the stapling head assembly is substantially uniform or non-uniform.

Example 17

The surgical instrument of any one or more of Examples 15 through Example 16, wherein the output displayed on the user interface comprises a color-coded indication conveying whether the load on the tissue compressed between the anvil and a deck surface of the stapling head assembly is substantially uniform.

Example 18

The surgical instrument of any one or more of Examples 15 through Example 17, wherein the output displayed on the user interface comprises a text indication conveying whether the load on the tissue compressed between the anvil and a deck surface of the stapling head assembly is substantially uniform.

Example 19

A surgical instrument comprising (a) a body assembly; (b) a shaft assembly extending distally from a distal end of the body assembly, (c) a stapling head assembly disposed at a distal end of the shaft assembly, wherein the stapling head assembly is operable to drive a plurality of staples into tissue, wherein the stapling head assembly comprises (i) an anvil-driving shaft configured to selectively move between a distal position and a proximal position within the shaft assembly, (ii) a body member, (iii) a deck surface connected with the body member, and (iv) one or more load cells positioned between the deck surface and the body member. The one or more load cells are configured to detect a parameter indicative of tissue loading between the anvil and the deck surface, wherein collectively the parameters detected are indicative of whether the tissue compressed between the anvil and the stapling head assembly is subject to a uniform or a non-uniform load. The instrument further comprises (d) an anvil selectively coupleable with the anvil-driving shaft, wherein the anvil is configured to move between the distal position and the proximal position when coupled with the anvil-driving shaft; and (e) a firing member configured to drive movement of the stapling head assembly to drive the plurality of staples into the tissue.

Example 20

A method uses a circular surgical stapler having (i) a body assembly, (ii) a shaft assembly extending distally from a distal end of the body assembly, (iii) a stapling head assembly, wherein the stapling head assembly is disposed at a distal end of the shaft assembly, wherein the stapling head assembly is operable to drive a plurality of staples into tissue, wherein the stapling head assembly includes an anvil-driving shaft configured to selectively move between a distal position and a proximal position within the shaft assembly, (iv) an anvil, wherein the anvil is selectively coupleable with the anvil-driving shaft, wherein the anvil is configured to move between the distal position and the proximal position when coupled with the trocar, (v) a plurality of sensors connected with the anvil and defining multiple loading zones, wherein each of the sensors is configured to detect a parameter for a respective one of the multiple loading zones indicative of tissue loading between the anvil and the stapling head assembly, and (vi) a firing member, wherein the firing member is configured to drive movement of the stapling head assembly to drive the plurality of staples into the tissue. The method comprises (a) locating the anvil, separate from a remainder of the surgical stapler, within a first severed end of a first portion of a tubular anatomical structure; (b) locating the stapling head assembly of the remainder of the surgical stapler within a second severed end of a second portion of the tubular anatomical structure; (c) attaching the anvil with the anvil-driving shaft; (d) retracting the anvil proximally toward the stapling head assembly to compress tissue between a deck surface of the stapling head assembly and the anvil; (e) confirming that the compressed tissue is subject to a uniform circumferential load by comparing the each of the parameters detected by each of the plurality of sensors for the respective loading zones with a predetermined threshold to ensure that none of the parameters exceed the predetermined threshold; (f) enabling actuation of the firing member only after the compressed tissue is subject to the uniform circumferential load according to (e); and (g) actuating the firing member to drive the plurality of staples into the tissue.

Example 21

The method of Example 20, further including (h) recording or storing the data associated with the parameter detected by each of the plurality of sensors; and (i) correlating the data from (h) with historical performance of the circular surgical stapler.

Example 22

The method of any one or more of Example 20 through Example 21, further including (j) recording or storing the data associated with the parameter detected by each of the plurality of sensors if not already completed; and (k) correlating the data from (j) with patient outcome data.

V. Miscellaneous

It should also be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

Furthermore, any one or more of the teachings herein may be combined with any one or more of the teachings disclosed in U.S. patent application Ser. No. 16/574,797, entitled "Method for Controlling Cutting Member Actuation for Powered Surgical Stapler," filed on Sep. 18, 2019; U.S. patent application Ser. No. 16/574,281, entitled "Method for Controlling End Effector Closure for Powered Surgical Stapler," filed on Sep. 18, 2019; U.S. patent application Ser. No. 16/574,299, entitled "Anvil Retention and Release Features for Powered Circular Surgical Stapler," filed on Sep. 18, 2019, issued as U.S. Pat. No. 11,185,331 on Nov. 30, 2021; and U.S. patent application Ser. No. 16/574,299, entitled "Compression and Firing Force Sensor for Circular Surgical Stapler," filed on even date herewith. The disclosure of each of these U.S. patent applications is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument comprising:
   (a) a body assembly, wherein the body assembly comprises a proximal end and a distal end;
   (b) a shaft assembly, wherein the shaft assembly extends distally from the distal end of the body assembly, wherein the shaft assembly comprises a proximal end and a distal end;
   (c) a stapling head assembly, wherein the stapling head assembly is disposed at the distal end of the shaft assembly, wherein the stapling head assembly is operable to drive a plurality of staples into tissue, wherein the stapling head assembly comprises an anvil-driving shaft configured to selectively move between a distal position and a proximal position within the shaft assembly;
   (d) an anvil, wherein the anvil is selectively coupleable with the anvil-driving shaft, wherein the anvil is configured to move between the distal position and the proximal position when coupled with the anvil-driving shaft, wherein the anvil comprises one or more sensors each configured to detect a parameter indicative of tissue loading between the anvil and the stapling head assembly;
   (e) a firing member, wherein the firing member is configured to drive movement of the stapling head assembly to drive the plurality of staples into the tissue; and
   (f) a processor, wherein each of the one or more sensors is in electrical communication with the processor and is configured to transmit one or more signals associated with the detected parameter to the processor, wherein the processor is configured to evaluate the one or more signals to determine whether a detected parameter exceeds a predetermined threshold when tissue captured between the anvil and the stapling head assembly is subject to a non-uniform load, wherein the predetermined threshold is based on the parameter detected by each of the one or more sensors.

2. The surgical instrument of claim 1, wherein the one or more sensors comprise three or more sensors.

3. The surgical instrument of claim 2, wherein the three or more sensors are located along the circumference of the anvil to define multiple loading zones.

4. The surgical instrument of claim 3, wherein each of the three or more sensors are associated with a respective one of the multiple loading zones, and wherein the parameter detected by each respective one of the three or more sensors is associated with the respective one of the multiple loading zones.

5. The surgical instrument of claim 1, wherein the one or more sensors comprise one or more strain gauges.

6. The surgical instrument of claim 5, wherein the parameter detected by the one or more strain gauges comprises a strain experienced by the anvil during tissue compression.

7. The surgical instrument of claim 1, wherein the one or more sensors comprise one or more proximity sensors.

8. The surgical instrument of claim 7, wherein the parameter detected by the one or more proximity sensors comprises a distance between the anvil and a deck surface of the stapling head assembly during tissue compression.

9. The surgical instrument of claim 1, wherein the one or more sensors comprise one or more load cells.

10. The surgical instrument of claim 9, wherein the parameter detected by the one or more load cells comprise a force applied to the tissue during tissue compression.

11. The surgical instrument of claim 1, wherein the predetermined threshold comprises a deviation from a median of the parameter detected by each of the one or more sensors.

12. The surgical instrument of claim 1, wherein the anvil further comprises one or more electrical contacts configured to transmit one or more signals from the one or more sensors from the anvil to a conductor extending through the stapling head assembly and the shaft assembly to the body assembly.

13. The surgical instrument of claim 12, wherein the processor is further configured to generate an output based on the signals, wherein the output is displayed on a user interface of the body assembly.

14. The surgical instrument of claim 13, wherein the output comprises an indication of whether the load on the tissue compressed between the anvil and a deck surface of the stapling head assembly is substantially uniform or non-uniform.

15. The surgical instrument of claim 13, wherein the output displayed on the user interface comprises a color-coded indication conveying whether the load on the tissue compressed between the anvil and a deck surface of the stapling head assembly is substantially uniform.

16. The surgical instrument of claim 13, wherein the output displayed on the user interface comprises a text indication conveying whether the load on the tissue compressed between the anvil and a deck surface of the stapling head assembly is substantially uniform.

17. The surgical instrument of claim 12, wherein the processor is housed in the body and is in electrical communication with the conductor.

18. The surgical instrument of claim 1, wherein the processor is further configured to generate an output based on the signals, wherein the output is configured to prevent the movement of the stapling head assembly.

19. A surgical instrument comprising:
 (a) a body assembly, wherein the body assembly comprises a processor, a proximal end and a distal end;
 (b) a shaft assembly, wherein the shaft assembly extends distally from the distal end of the body assembly, wherein the shaft assembly comprises a proximal end and a distal end;
 (c) a stapling head assembly, wherein the stapling head assembly is disposed at the distal end of the shaft assembly, wherein the stapling head assembly is operable to drive a plurality of staples into tissue, wherein the stapling head assembly comprises:
  an anvil-driving shaft configured to selectively move between a distal position and a proximal position within the shaft assembly,
  (ii) a body member,
  (iii) a deck surface connected with the body member, and
  (iv) one or more sensors positioned between the deck surface and the body member, wherein each of the one or more sensors is configured to detect a parameter indicative of tissue loading between the anvil and the deck surface;
 (d) an anvil, wherein the anvil is selectively coupleable with the anvil-driving shaft, wherein the anvil is configured to move between the distal position and the proximal position when coupled with the anvil-driving shaft; and
 (e) a firing member, wherein the firing member is configured to drive movement of the stapling head assembly to drive the plurality of staples into the tissue,
 wherein each of the one or more sensors is in electrical communication with the processor and is configured to transmit one or more signals associated with the detected parameter to the processor,
 wherein the processor is configured to evaluate the one or more signals to determine whether a detected parameter exceeds a predetermined threshold when tissue captured between the anvil and the stapling head assembly is subject to a non-uniform load,
 wherein the predetermined threshold is based on the parameter detected by each of the one or more sensors.

20. A method of using a circular surgical stapler having (i) a body assembly, (ii) a shaft assembly extending distally from a distal end of the body assembly, (iii) a stapling head assembly, wherein the stapling head assembly is disposed at a distal end of the shaft assembly, wherein the stapling head assembly is operable to drive a plurality of staples into tissue, wherein the stapling head assembly includes an anvil-driving shaft configured to selectively move between a distal position and a proximal position within the shaft assembly, (iv) an anvil, wherein the anvil is selectively coupleable with the anvil-driving shaft, wherein the anvil is configured to move between the distal position and the proximal position when coupled with the anvil-driving shaft, (v) a plurality of sensors connected with the anvil and defining multiple loading zones, wherein each of the sensors is configured to detect a parameter for a respective one of the multiple loading zones indicative of tissue loading between the anvil and the stapling head assembly, and (vi) a firing member, wherein the firing member is configured to drive movement of the stapling head assembly to drive the plurality of staples into the tissue, the method comprising:
 (a) locating the anvil, separate from a remainder of the surgical stapler, within a first severed end of a first portion of a tubular anatomical structure;
 (b) locating the stapling head assembly of the remainder of the surgical stapler within a second severed end of a second portion of the tubular anatomical structure;
 (c) attaching the anvil with the anvil-driving shaft;
 (d) retracting the anvil proximally toward the stapling head assembly to compress tissue between a deck surface of the stapling head assembly and the anvil;
 (e) confirming that the compressed tissue is subject to a uniform circumferential load by comparing the each of the parameters detected by each of the plurality of sensors for the respective loading zones with a predetermined threshold to ensure that none of the parameters exceed the predetermined threshold;
 (f) enabling actuation of the firing member only after the compressed tissue is subject to the uniform circumferential load according to (e); and
 (g) actuating the firing member to drive the plurality of staples into the tissue.

* * * * *